United States Patent [19]
Walker et al.

[11] Patent Number: 5,622,836
[45] Date of Patent: Apr. 22, 1997

[54] MONOCLONAL ANTIBODIES WHICH RECOGNIZE MALIGNANT CELLS FROM BLADDER CARCINOMAS

[75] Inventors: Karen Z. Walker, Coogee; Pamela J. Russell, Wahroonga, both of Australia

[73] Assignees: The University of Sydney; The Central Sydney Area Health Service, both of New South Wales, Australia

[21] Appl. No.: 261,009

[22] Filed: Jun. 14, 1994

Related U.S. Application Data

[63] Continuation of Ser. No. 793,367, filed as PCT/AU90/00218, May 24, 1990, abandoned.

[30] Foreign Application Priority Data

May 24, 1989 [AU] Australia ................... PJ4351
May 24, 1990 [WO] WIPO ................ PCT/AU90/00218

[51] Int. Cl.$^6$ .................. C07K 16/28; C07K 16/30; C12N 5/12
[52] U.S. Cl. .............. 435/344; 435/70.21; 435/70.2; 435/328; 435/344.1; 530/391.3; 530/388.85; 530/388.8; 530/387.3
[58] Field of Search ............... 530/388.8, 388.85, 530/391.3, 387.3; 435/70.21, 70.2, 240.27

[56] References Cited

U.S. PATENT DOCUMENTS 4,643,971 2/1987 Fradet et al. ..................... 435/240

OTHER PUBLICATIONS

Harris et al., TIBTECH, 11:42, 1993, Therapeutic ... Age.
Waldmann, Monoclonal Ab . . . Therapy, Science, 1991, 252:1657–62.
Walker et al, Detection of . . . Assay, J. Urol., 1989, 142:1578–83.
Bander NH., Monoclonal Antibodies In Urologic Oncology. Cancer 60:658–667 (1987).
Boniface GR, Izard ME, Walker KZ, McKay DR, Sorby PJ, Turner JH and Morris JG. Labelling of monoclonal antibodies with Samarium–153 for combined radioimmunoscintigraphy and radioimmunotherapy. J. Nucl. Med. 30(5):683–691 (1989).
Chopin DK, deKernion JB, Rosenthal DL and Fahey JL. Monoclonal antibodies against transitional cell carcinoma for detection of malignant urothelial cells in bladder washing. J. Urol. 134:260.265 (1985).
Cloutier RJ and Watson EE. Radiation dose from radioisotopes in the blood. In *Medical Radionuclides: radiation dose and effects*, ORNLC 691212. Eds: Cloutier RJ, Edwards CL and Snyder WS. Oak Ridge National Laboratory, Oak Ridge. pp. 325.346 (1970).
Early PJ and Sodee DB. Dosimetry. In: Principles and Practice of Nuclear Medicine. CV Mosby Co, Toronto. pp. 113–130 (1985).
Edwards PAW, Smith CM, Neville AM and O'Hare MJ. A human–human hybridoma system based on a fast–growing mutant of the ARH.77 plasma cell leukemiadeviced line. Eur. J. Immunol. 12:641–648 (1982).
Feller PA and Sodd VJ. Dosimetry of four heart imaging radionuclides: 43K, 81Rb, 129Cs and 201Tl J. Nucl. Med. 16(11):1070.1075 (1975).
Hakomori S. Tumor–associated carbohydrate antigens. Ann. Rev. Immunol. 2:103.126 (1984).
Huland H, Otto U and Droese M. The value of urinary cytology, serum and urinary carcinoembryonic antigen, rheumatoid factors, and urinary immunoglobulin concentration as tumour markers or prognostic factors in predicting progression of superficial bladder cancer. Eur. Urol. 9:346.349 (1983).
Köhler G and Milstein C. Derivation of specific antibody–producing tissue culture and tumour lines by cell fusion. Eur. J. Immunol. 6:511.519 (1976).
Ledeen RW and Yu RK. Gangliosides: structure, isolation and analysis. Meth. Enzymol. 83:139–191 (1982).
Limas C and Lange P. Altered reactivity for A, B, H antigens in transitional cell carcinomas of urinary bladder. A study of the mechanisms involved. Cancer 46:1366.1373 (1980).
Longin A, Huazi A, Berger.Dutrieux N, Escourrou G, Bouvier R, Richer G, Mironneau I, Fontaniere B, Devonec M and Laurent JC. A monoclonal antibody (BL2.10Dl) reacting with a bladder cancer.associated antigen. Int. J. Cancer 43:183.189 (1989).
Magnani JL, Brockhaus M, Smith DF, Ginsburg V, Blaszczyk M, Mitchell KF, Steplewski Z and Koprowski H. A mosialoganglioside is a monoclonal antibody–defined antigen of color carcinoma. Science 212:55.56 (1981).
Masuko T, Yagita H and Hashimoto Y. Monoclonal antibodies against cell surface antigens present on human urinary bladder cancer cells. J. Nat. Cancer Inst. 72(3):523.530 (1984).
McCabe RP, Haspel MV, Potamo N and Hanna MG. Monoclonal antibodies in the detection of bladder cancer. In *Cancer Diagnosis In Vitro using Monoclonal Antibodies* Ed. HZ Kupchik. Marcel Dekker Inc., New York. pp. 1.29 (1988).
Murphy WM, Soloway MS, Jukkola AF, Crabtree WN and Ford KS. Urinary cytology and bladder cancer. The cellular features of transitional cell neoplasms. Cancer 53:1555.1565 (1984).

(List continued on next page.)

Primary Examiner—Frank C. Eisenschenk
Attorney, Agent, or Firm—Foley & Lardner

[57] ABSTRACT

The present invention relates to a family of novel antigens associated with malignant cells of bladder carcinomas, and to antibodies, portions or fragments thereof, or single domain antibodies which recognize those antigens. The invention provides methods of detecting bladder carcinomas using those antibodies, fragments or portions thereof, or single domain antibodies, to kits for use in those methods and to methods of treating bladder carcinoma using the antibodies, fragments or portions thereof, or single domain antibodies.

26 Claims, 14 Drawing Sheets

OTHER PUBLICATIONS

Myers, M.J. Dosimetry for radiolabelled antibodies—macro or micro? Int. J. Cancer. Supplement 2, 71.73 (1988).

Piccoli G, Varese D and Rotienno M. Diagnosis and clinical correlations in Nephrology. In: *Atlas of Urinary Sediments*. Raven Press, New York. pp. 48.49 (1984).

Ridell M, Minnikin DE, Partlett JH and Mattsby–Baltzer I. Detection of mycobacterial lipid antigens by a combination of thin–layer chromatography and immunostaining. Lett. Appl. Microbiol. 2:89.9210 (1986).

Russell PJ, Raghavan D, Gregory P, Phillips J, Wills EJ, Jelbart M, Wass J, Zbroja RA and Vincent PC. Bladder cancer xenografts: a model of tumour cell heterogeneity. Cancer Res. 46:2035–2040 (1986).

Russel PJ, Jelbart ME, Wills E, Singh S, Wass J, Wotherspoon J and Raghavan D. Establishment and characterization of a new human bladder cancer cell line showing features of squamous and glandular differentiation. Int. J. Cancer 41:74.82 (1988).

Russell PJ, Raghavan D, Philips J and Wills EJ. The biology of urothelial cancer. In The Management of Bladder Cancer. Ed. D Raghavan, Edward Arnold Publishers, London. pp. 1–41 (1988a).

Russell PJ, Wills EJ, Philips J, Jelbart M, Gregory P and Raghavan D. Features of squamous and adenocarcinoma in the same cell in a xenografted human transitional cell carcinoma: Evidence of a common histogenesis? Urol. Res. 16:79.84 (1988b).

Russell PJ, Wass J, Lukeis R, Garson OM, Jelbart M, Wills E, Philips J, Brown J, Carrington N, Vincent PC and Raghavan D. Characterisation of cell lines derived from a multiply aneuploid human bladder transitional–cell carcinoma, UCRU.BL.13.Int. J. Cancer. 44:276.285 (1989).

Sharkey RM, Kaltovich FA, Shih LB, F and I, Govelitz G and Goldenberg DM. Radioimmunotherapy of human colonic cancer xenografts with 90Y.labeled monoclonal antibodies to carcinoembryonic antigen. Cancer Res. 48:3270.3275 (1988).

Snyder WS, Ford MR, Warner GG and Watson SB. A tabulation of dose equivalent per microcurie–day for source and target organs of an adult for various radionuclides. In : *ORNL*.500. Oak Ridge National Laboratory, Oak Ridge. p. 3 (1974).

van Haafen.Day C, Russell P, Rugg C, Wills EJ and Tattersall MHN. Flow cytometric and morphological20 studies of ovarian carcinoma cell lines and xenografts. Cancer Res. 43:3725.3731 (1983).

van Haafen.Day C, Russell P, Carr S and Wright L. Development and characterization of a human cell line from an ovarian mixed mullerian tumor (carcinosarcoma). In Vitro Cell Dev. Biol. 24(10):965.971 (1988).

Vartdal F, Vandvik B and Lea T. Immunofluorescence staining of agarose.embedded cells. A new technique developed for immunological characterization of markers on a small number of cells. J. Immunol. Meth. 92:125.129 (1986).

Walker KZ, Gibson J, Axiak SM and Prentice RL. Potentiation of hybridoma production by the use of mouse fibroblast conditioned media. J. Immunol. Methods 88:75.81 (1986).

Walker KZ, Seymour.Munn K, Keech FK, Axiak SM, Bautovich GJ, Morris JG and Basten A. A rat model system for radioimmunodetection of kapp myeloma antigen on malignant B cells. Eur. J. Nucl. Med. 12:461.467 (1986).

Ward ES, Gaussan D, Griffiths AD, Jones PT and Winter G. Binding activities of a repertoire Of single immunoglobulin variable domains secreted from *Escherichia coli*. Nature 341:544.546 (1989).

Zola H, Moore HA, Hunter IK and Bradley J. Analysis of chemical and biochemical properties of membrane molecules in situ by analytical flow cytometry with monoclonal antibodies. J. Immunol. Meth. 74:65.77 (1984a).

Zola H, Moore HA, Hohmann A, Hunter IK, Nikoloutsopoulos A and Bradley J. The antigen of mature human B cells detected by the monoclonal antibody FMC7 studies of the nature of the antigen and 20 modulation of its expression. J. Immunol. 133(1):321.326 (1984b).

Lightfoot et al., "Dosimetric and Therapeutic Studies in Nude Mice Xenograft Models with $^{153}$Samarium–Labelled Monoclonal Antibody, BLCA–38", Antibody, Immunoconjugates, And Radiopharmaceuticals, vol. 4, No. 3, (1991).

Patent Abstracts of Japan, C–601, p. 5, JP.A. 1–40500 (Takashi Masuko) 10 Feb. 1989.

Patent Abstracts of Japan, C–561, p. 105, JP.A. 63–230096 (Sumitomo Electric Ind Ltd) 26 Sep. 1988.

Fradet et al., "Polymorphic expression of a human superficial bladder tumor antigen defined by mouse monoclonal antibodies", pp. 7227–7231, Proceedings of the National Academy of Science, USA, vol. 84, (1987).

Braesch–Andersen et al., "Isolation and characterization of two bladder carcinoma–associated antigens", pp. 145–151, Journal of Immunological Methods, vol. 94, (1986).

Young et al., "Production and Characterization of Mouse Monoclonal Antibodies to Human Bladder Tumor–associated Antigens", pp. 4439–4446, Cancer Research, vol. 45, (1985).

Hellstrom et al., "Monoclonal Antibodies to Cell Surface Antigens Shared by Chemically Induced Mouse Bladder Carcinomas", pp. 2210–2218, Cancer Research, vol. 45, (May 1985).

Trejdosiewicz et al., "Monoclonal Antibodies to Human Urothelial Cell Lines and Hybrids: Production and Characterization", pp. 533–538, Journal of Urology, vol. 133, No. 3, (Mar. 1985).

Burbenik et al., "Monoclonal Antibodies against Human Urinary Bladder Carcinomas: Selectivity and Utilization for Gamma Scintigraphy", pp. 701–710, European Journal of Cancer and Clinical Oncology, vol. 21, No. 6, (1985).

Masuko et al., "Monoclonal Antibodies Against Cell Surface Antigens Present on Human Urinary Bladder Cancer Cells", pp. 523–530, Journal of the Natural Cancer Institute, vol. 72, No. 2, (Mar. 1984).

Kohwi et al., "Amphipathic Lipid–Bound Protein Antigens in Mouse Bladder Carcinomas Detected by a Monoclonal Antibody", pp. 5945–5950, Biochemistry, vol. 23, No. 25, (1984).

Grossman, H. Barton, "Hybridoma Antibodies Reactive With Human Bladder Carcinoma Cell Surface Antigens", pp. 610–614, Journal of Urology, vol. 130, (1983).

Bubbers et al., "Hybridoma Antibodies Detecting Human Transitional Cell Carcinoma (TCC) Antigens on Murine Cells Transfected With Human TCC DNA", p. 225, Proceedings of the American Association of Cancer Research, vol. 24, No. 74, (1983).

Takenaka et al., "Monoclonal antibody to desmosome associated 34kD protein and immunohistochemical study in relation to the malignancy of transitional cell carcinomas of urinary bladder", p. 551, Col. 1, Abstract No. 176653k, Nippon Hinyokika Gakkai Zasshi, 1989, (80)12, 1769–75 (Japan), Chemical Abstracts, vol. 112, No. 19, (May 7, 1990), (Columbus, Ohio USA).

Zhang et al., "Immunochemical and Biochemical Characterizations of Two Monoclonal Antibody-reacting Antigens Associated with Human Bladder Carcinoma", pp. 6621–6628, Cancer Research, vol. 49, (1989).

Hill et al., C.R. Hill, Chpt. 2.3 in Monoclonal Antibodies: Principles and Applications, pp. 121–136, 1995.

LOG FLUORESCENCE

LOG FLUORESCENCE

500
MONOCLONAL ANTIBODIES WHICH RECOGNIZE MALIGNANT CELLS FROM BLADDER CARCINOMAS

This application is a continuation of application Ser. No. 07/793,367, filed as PCT/AU90/00218, May 24, 1990 now abandoned.

TECHNICAL FIELD

This invention relates to antibodies, single domain antibodies and portions or fragments of the antibodies directed against malignant cells in the urine of patients suffering from bladder carcinoma, to the cell lines producing those antibodies, or single domain antibodies to diagnostic assays using the antibodies, single domain antibodies or portions or fragments of the antibodies and to compositions and kits comprising the antibodies, single domain antibodies, or portions or fragments of the antibodies. The antibodies, single domain antibodies, or portions or fragments of the antibodies have both diagnostic and therapeutic utility.

BACKGROUND ART

Early detection of bladder cancer remains an important problem in management of bladder cancer. Urinary cytology with specificity and sensitivity of 50–80% (Murphy et al., 1984) is hampered by subjective observer error, the importance of processing techniques, and artefacts introduced by inflammation or chemotherapy (Chopin et al., 1985). More recently developed methods have not resolved the aforementioned problems. For example, flow cytometry (for review, see Russell et al., 1988a) requires substantial equipment and a large number of shed cells. Furthermore, the correlation between ploidy and prognosis is imperfect. Similarly, immunohistological staining for ABO blood group antigens or the T-(Thomsen Freidenreich) antigen (Limas and Lange, 1980) or carcinoembryonic antigen (Huland et al., 1983) gives variable correlation with prognosis and has major limitations for early diagnosis of new or recurrent disease.

Recently, more useful tumour markers have been identified by using monoclonal antibodies raised against bladder carcinomas. These have been used to detect bladder cancer cells in bladder washings (Chopin et al., 1985).

DESCRIPTION OF THE INVENTION

The present inventors have discovered a family of novel antigens detectable in urine and found in patients with bladder carcinoma.

The discovery of these antigens and the development of antibodies which recognise them has enabled the development of diagnostic and therapeutic methods for the detection and treatment of bladder carcinoma employing the antibodies against the antigens, or single domain antibodies against the antigens, or portions or fragments of the antibodies.

The present invention has advantages over the conventional methods for detection of bladder cancer in that the use of voided urine samples, rather than bladder washings, is non-invasive and does not require any surgical procedure. It is a relatively simple, cost effective, highly specific technique, not requiring a high level of cytopathological skill for interpretation, and can be completed on the day of receipt of the sample. Moreover, the percentage of positive results is much higher than that which can be obtained by conventional cytological analysis of the urine.

According to a first embodiment of the present invention there is provided a cell line producing an antibody or single domain antibody directed against an antigen of malignant cells associated with bladder carcinoma, which antigen is found in voided urine of bladder carcinoma patients.

According to a second embodiment of the present invention there is provided an antibody, or antigen binding fragment or portion thereof, or a single domain antibody reactive with an antigen of malignant cells associated with bladder carcinoma which antigen is found in the voided urine of bladder carcinoma patients.

According to a third embodiment of the present invention there is provided an antibody composition comprising at least one antibody, or antigen binding fragment or portion thereof, or single domain antibody of the second embodiment together with a pharmaceutically acceptable carrier or diluent.

According to a fourth embodiment of the present invention there is provided a method for the detection of bladder carcinoma, which method comprises the steps of:

(a) contacting a sample of cells obtained from voided urine of a subject suspected to be suffering from bladder carcinoma with an antibody or antigen binding fragment or portion thereof or single domain antibody of the second embodiment labelled with a detectable marker;

(b) incubating the cells and the labelled antibody or antigen binding fragment or portion thereof or single domain antibody to permit the labelled antibody or antigen binding fragment or portion thereof or single domain antibody to bind to bladder carcinoma cells present in the sample; and (c) detecting the labelled cells.

In one form of the present invention there is provided a method for the detection of bladder carcinoma, which method comprises detecting the presence of an antigen recognised by an antibody, fragment or portion thereof or a single domain antibody of the second embodiment in voided urine from a patient suspected to be suffering from bladder carcinoma.

According to a fifth embodiment of the present invention there is provided a kit for the detection of bladder carcinoma which kit comprises:

at least one antibody, or antigen binding fragment or portion thereof, or single domain antibody according to the second embodiment together with a positive and/or negative control.

According to a sixth embodiment of the present invention there is provided a method of tumour therapy which method comprises the administration of an antibody, or antigen binding fragment or portion thereof, or single domain antibody of the second embodiment, or an antibody composition of the third embodiment to a host in need of such treatment where the antibody, or antigen binding fragment or portion thereof, or single domain antibody is labelled with a radiolabel, immunotoxin or a cytotoxic drug. The antibody, or antigen binding fragment or portion thereof, or single domain antibody is used to target the radiolabel, immunotoxin or cytotoxic drug to the tumour.

The cell line of the present invention is preferably an immortal cell line, such as a hybridoma cell line. Typically hybridoma cell lines are produced by the fusion of an antibody-producing cell with a myeloma cell.

The cell line may also be a recombinant cell line such as a bacterial or eukaryotic cell line expressing a foreign gene encoding a single domain antibody directed against an antigen of malignant cells associated with bladder carcinoma, which antigen is found in voided urine of bladder carcinoma patients.

Preferably, the malignant cells with which the antigen is associated are cells from a transitional cell carcinoma (TCC) of the bladder.

Preferably, the antigen found in the voided urine of the patient is stable in the voided urine of the patient.

According to one preferred form of the present invention the antigen is a neutral glycolipid.

In another preferred form of the present invention, the antigen is a protein.

It is preferred that the antibody is an $IgG_3$ antibody.

Preferably the antibody, antigen-binding fragment or portion thereof, or single domain antibody is directed against a TCC cell line selected from the group consisting of UCRU-BL-17-CL, UCRU-BL-23/3, UCRU-BL-13/0 and 5637 as herein described.

Preferably, the cell line is a hybridoma cell line selected from BLCA-8, BLCA-30 and BLCA-38 as herein described.

More preferably the hybridoma cell line is BLCA-8. BLCA-8 was deposited with the American Type Culture Collection of 12301 Parklawn Drive, Rockville, Md. 20852, USA on 14 Feb. 1990 under accession number HB 10406.

The antibody, or antigen-binding fragment or portion thereof, or single domain antibody is typically used for diagnostic or therapeutic purposes in labelled form.

Typical labels include fluorescent labels, radiolabels and enzyme labels.

Labelling may also be by means of a second antibody against the antibody, fragment or portion thereof, or single domain antibody.

The second antibody in turn is labelled with a detectable label such as an enzyme, radiolabel or fluorescent label.

The use of amplification systems such as biotin-avidin associated labelling systems to achieve amplification of the signal to be detected is also encompassed by the present invention.

A preferred fluorescent label of the present invention is fluorescein isothiocyanate.

Typical pharmaceutically acceptable carriers or diluents used in the preparation of antibody compositions of the present invention include isotonic buffered saline solutions such as PBS or TBS, and tissue culture media.

In the detection method of the fourth embodiment any suitable detection procedure for detecting labelled cells may be employed.

Preferred procedures include: fluorescent immunoassay; enzyme immunoassay, such as ELISA; radioimmunoassay, agglutination assay and combination thereof.

The procedure may involve the use of a second antibody and may involve the use of an amplification system such as a biotin-avidin system.

Preferably, the preparation of bladder cells is prepared by centrifuging a urine sample of a patient thought to be suffering from bladder carcinoma, collecting the cells, embedding the cells in agarose and staining the cells with a labelled antibody, fragment or portion thereof or a single domain antibody of the present invention.

Where a kit according to the present invention comprises an enzyme labelled antibody, portion or fragment thereof, or single domain antibody, the kit also preferably includes a substrate for that enzyme.

Cytotoxic drugs suitable for labelling an antibody, fragment or portion thereof, or single domain antibody for use in therapy include Vinblastine, Iadarubicin, Aminopterin, Methotrexate or 5-Fluorodeoxyuridine.

Immunotoxins include Pseudomonas exotoxin or ricin. Radiolabels include 131-Iodine, 153-Samarium, 90-Yttrium, 186-Rhenium, 211-Astatine and 67-Copper.

The labelled antibody, fragment or portion thereof, or single domain antibody may be administered systemically or directly into the bladder through its orifice.

DEFINITIONS

Stability of the antigen

Throughout the specification and claims, reference to the antigen recognised as "stable" in voided urine means that greater than 50% of the antigen is still detectable after 18 hours exposure to urine.

Fragments and portions of antibodies

Throughout the specification and claims reference to an antigen-binding fragment or portion of an antibody encompasses those fragments and portions capable of binding to the antigen recognised by the antibody. It includes for instance, Fab and $(Fab')_2$ fragments. The antigens recognised by antibodies of this invention are antigens of malignant cells associated with bladder carcinoma, and found in the voided urine of bladder carcinoma patients.

ABBREVIATIONS

FITC—fluorescein isothiocyanate

SaMIg—sheep anti-mouse immunoglobulins

BLCA—bladder cancer

UCRU—Urological Cancer Research Unit.

MAbs—monoclonal antibodies

TCC—transitional cell carcinoma

BL-17—UCRU-BL-17

BL-23—UCRU-BL-23 CL

SaMIg-FITC—fluorescein isothiocyanate conjugated anti-mouse sheep immunoglobulin SN—supernatant TBS—0.03 Tris, 0.9% sodium chloride, pH 7.2

PBS—0.14M NaCl, 2.7 mM KCl, 8 mM $Na_2HPO_4$ 0.7 mm $KH_2PO_4$, pH 7.2

PBS/Az—PBS with 0.02% sodium azide

SA-HRP—streptavidin conjugated horseradish peroxidase

2-ME—2-mercaptoethanol $Le^y$—Lewis$^y$ antigen $Le^a$—Lewis$^a$ antigen $Le^b$—Lewis$^b$ antigen $Le^x$—Lewis$^x$ antigen O/N—overnight BSA—bovine serum albumin SaMIg-B—biotinylated sheep anti-mouse immunoglobulin A-AP—avidin conjugated alkaline phosphatase TLC—thin layer chromatography ELISA—enzyme-linked immunosorbant assay $PBS/CaCl_2$—PBS with 0.5 mM $CaCl_2$ GS-I—*Griffonia simplicifolia* lectin DBA—*Dolichos biflorus* lectin
SBA—Soy Bean agglutinin (*Glycine max* lectin)
WGA—Wheatgerm agglutinin
Con A—Concanavalin A (*Canavalia ensiformis* lectin)
UEA-1—*Ulex europaeus* lectin
TBS/CaCl$_2$—5 mM Tris, 15 mM NaCl, 1 mM CaCl$_2$
$^{125}$I-SaMIg—$^{125}$Iodine-labelled sheep anti-mouse immunoglobulin
OD—optical density

BRIEF DESCRIPTION OF THE DRAWINGS

Preferred embodiments of the present invention will now be described by way of Example only with reference to the following non-limiting examples and to the drawings wherein:

FIG. 9A shows the binding of BLCA-8 (solid line) or BLCA-7 control Mab (interrupted line) in an ELISA. MAbs were tested either against a lipid extract prepared from BL-23 cells ( ) or against ganglioside G$_{M1}$ ( ).

In both 9A and 9B, the horizontal axis indicates the concentration of antigen in μg per ml from which 50 μl per well was added to the plate.

Figure 10:
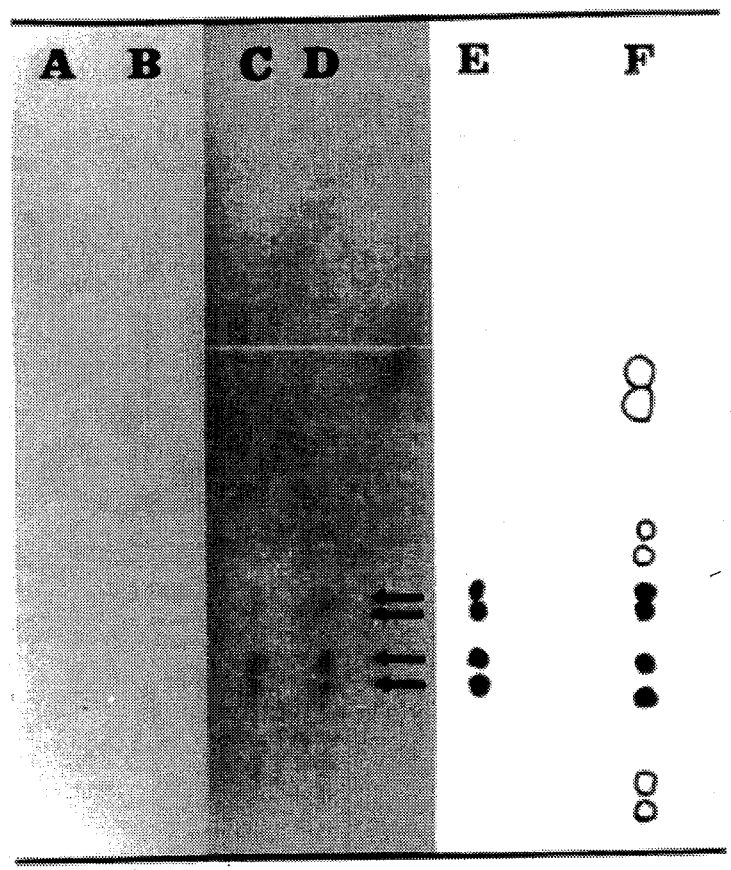
Figure 11A:
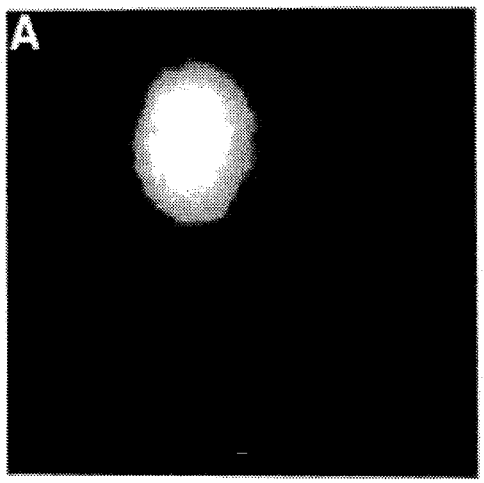
Figure 11B:
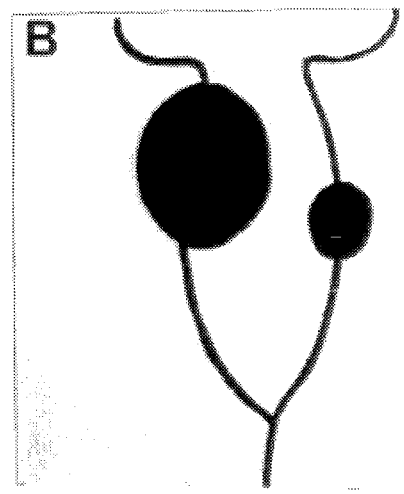
Figure 11C:
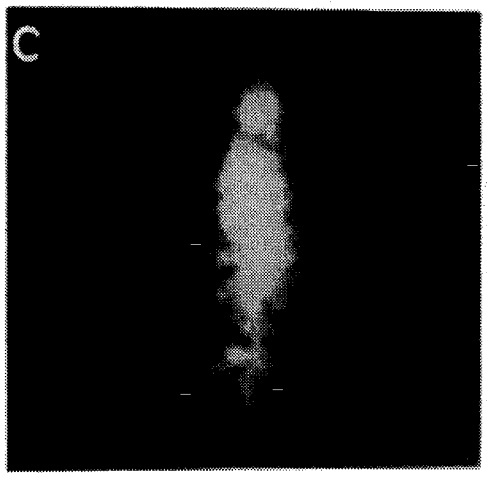
Figure 11D:
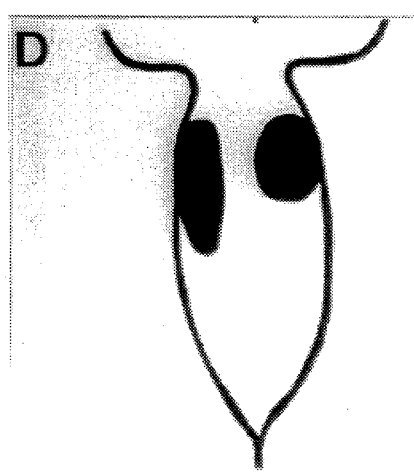

FIG. 10: Shows immunoblotting of control MAb, K-1-21 (A,B) or test MAb, BLCA-8 (C,D) to a TLC separation from a BL-23 lipid extract. Six μl (A,C) or 9 μl (B,C) of extract was applied to the plate. Arrows and a pen trace (E) indicate components specifically bound by BLCA-8. Track F indicates lipids visualised with α-naphthol. Components with equivalent migration to the BLCA-8 reactive components shown in E are in solid colour.

FIG. 11: Shows images from tumour bearing mice injected with $^{131}$I-BLCA-38 or control MAb. Nude mice bearing BL-17 xenografts were injected with $^{131}$I-BLCA-38 (A,B) or $^{131}$I-L7 (control) MAb (C,D). A and C represent gamma camera images taken from these animals 7 days after conjugate injection whereas B and D indicate the position of the subcutaneous xenografted tumours in the individual animals.

FIG. 12: Shows the growth of BL-17 human bladder cancer xenografts (A and B) or Jo. N. human ovarian cancer xenografts (C and D) after injection of a $^{153}$Samarium-labelled control antibody (A and C) or $^{153}$Sm-BLCA-38 (B and D): healthy tumour tissue: widespread tumour necrosis.

FIG. 13: Shows the change in the log percent initial tumour volume after a single injection of:
A) unlabelled BLCA-38 (0) or saline (0)
B) $^{131}$1-BLCA-38 (0) or $^{131}$1 control MAb (0)
C) $^{153}$1-BLCA-38 (0) or $^{153}$Sm control MAb (0)

BEST METHOD OF CARRYING OUT THE INVENTION

It is established that by cloning of the gene sequence encoding the antigen binding pocket of a monoclonal antibody a single domain antibody can be produced which will bind to the antigen recognised by the monoclonal antibody (Ward et al. 1989). Thus using standard techniques a cell line can be established which expresses a single domain antibody which recognises a bladder carcinoma antigen found in the voided urine of patients when one is provided with a monoclonal antibody of the present invention.

Further, it is known that antibodies can be digested with papain to produce Fab fragments and with pepsin to produce (Fab')$_2$ fragments both of which are capable of binding to antigens recognised by the antibodies from which they are derived.

The monoclonal antibodies of the present invention are prepared by standard techniques. These are described in (Walker et al. 1986). The monoclonal antibodies are either present in the supernatant taken from hybridoma cell culture or they are purified by standard techniques.

Antibody compositions of the present invention are prepared by admixing purified antibodies, antigen-binding fragments or portions thereof, or single domain antibodies of the invention with a pharmaceutically acceptable carrier or diluent using standard methods of pharmaceutical preparation. Typically the carrier or diluent is selected from isotonic buffered salines or tissue culture media.

Diagnostic kits are prepared by formulating antibodies, antigen-binding fragments or portions thereof, or single domain antibodies at appropriate concentration to the antigen to be detected with a pharmaceutically acceptable carrier or diluent. A positive control standard of a known concentration of the antigen to be detected is prepared similarly. The negative standard comprises carrier or diluent alone or an antigen of irrelevant specificity diluted with a pharmaceutically acceptable carrier or diluent. The antibody, antigen-binding fragment or portion thereof, or single domain antibody is provided in labelled form or alternatively the label is provided separately in the kit.

Therapeutic administration of antibodies, antigen-binding fragments or portions thereof, or single domain antibody or antibody compositions for targetting tumours is in accordance with standard techniques. The antibodies, antigen-binding fragments or portions thereof, or single domain antibody are used to target radioisotopes, immunotoxins or cytotoxic drugs with which they are labelled, to the tumour. This method is particularly suited for use with bladder cancers since the bladder has an opening to the external surfaces of the patient through which the antibody can be administered thus avoiding the need for intravenous administration.

Human cancer cell lines

The following human cancer cell lines were studied: (i) Human bladder cancer: UCRU-BL-17-CL (Russell et al., 1988), UCRU-BL-13 (Russell et al. 1989), UCRU-BL-23/3 (Russell et al. unpublished) and 5637 (obtained from The American Type Culture Collection USA). The BL-23/3 bladder cancer cell line was established in the Urological Cancer Research Unit, Royal Prince Alfred Hospital by Dr Pam Russell and Ms Zambela Palavidis from the second passage of the xenografted cell line UCRU-BL-17. The original tumour was obtained from a 69 year old female, blood group A, who presented with a grade III stage 4b transitional cell carcinoma of the bladder. The xenograft was established before treatment of the patient. Flow cytometric analysis revealed a diploid tumour with a tetraploid peak. The cell line is tumourogenic in nude mice and has 57–66 human chromosomes. Clonal abnormalities include deletion 1p, derivative 3q, translocation between 1q and 6q, deletion 6q, insertion 11p, +7, −16, and 2 metacentric markers (ii) Human ovarian cancer: GV, JoN, GG, MW and NF (van Haaften-Day et al., 1983), from Dr. C. van Haaften-Day, Ludwig Institute of Cancer Research, Sydney (iii) Human Colonic Cancer, LIM 1215, LIM 1839 and LIM 2099, from Dr. R. Whitehead, Ludwig Institute of Cancer Research, Melbourne and Colot, from Dr. C. van Haaften-Day; (iv) Human melanoma lines: MM170, PMC 22B, MM 253cl, MM 96E and MM418E, from Dr. J. Pope, Queensland Institute of Medical Research, Brisbane; (v) Human lymphoid and leukemic lines: CCRF-CEM, MOLT-4, F2/F7, Daudi, JP, TBJ, RDG and BMG, from Ludwig Institute of Cancer Research, Sydney; U266-BL, JOK-1, and JOK-2 from Dr. H. Zola, Flinders Medical Centre, Adelaide, WI-L2-729-HF2from Dr. J. Heitzmann, The Salk Institute, San Diego, Calif.; Ludwig Institute of Cancer Research (LON) HMy2 (Edwards et al., 1982) from Ludwig Institute of Cancer Research, London; HL60 and K562 from the American Type Culture Collection.

The bladder lines were maintained at 37° C. in 5% $O_2$, 7.5% $CO_2$ and 87.5% $N_2$, whilst all other lines were incubated in 7.5% $CO_2$ in air. Medium for all lines was RPMI 1640 (Flow Laboratories, North Ryde, Sydney, Australia), supplemented with 10% foetal calf serum (FCS) (Commonwealth Serum Laboratories, Melbourne, Australia) which had been heated to 56° C. for 30 mins. Cells were fed twice weekly, and were passaged using 0.25% trypsin (Flow Laboratories) or 1 mM ethylene diamine tetraacetic acid (EDTA, Flow Laboratories).

EXAMPLE 1—Murine monoclonal antibodies from mice immunised with the UCRU-BL-17CL human bladder cancer cell line A panel of 3 murine MAbs: BLCA-8, −30, and −38 was developed in the Clinical Immunology Research Centre, University of Sydney (CIRCUS). BALB/c mice were immunised with multiple intraperitoneal (i.p.) injections of the human bladder TCC line, BL-17 and derived xenografts. The immune spleen cells were fused with NSI-1 Ag4.1 mouse myeloma cells (Kohler et al. 1976) and cultured as described previously (Walker et al. 1986). MAb K-1-21 of irrelevant specificity was used as a negative control while the MAb BB7.7 (from the American Type Culture Collection) reactive against human HLA-A,B,C antigens acted as a positive control. Monoclonal antibodies were used either as supernatants from the hybridoma cell cultures or they were affinity purified on Protein A using standard techniques. Antibody isotypes were determined by reactivity with subclass specific antisera. BLCA-8 and BLCA-30 are of the $IgG_3$ subclass while BLCA-38 is an $IgG_1$ antibody.

EXAMPLE 2—Reactivity of murine monoclonal antibodies with normal and malignant cells The reactivity of the panel of murine MAb described in Example 1 with normal and malignant cells was examined. Three different methods were employed.

a) Flow cytometric analysis of surface immunofluorescence

Cultured cells were harvested with 1 mM EDTA, washed once in Dulbecco PBS, containing 0.02% sodium azide (BDH Chemicals Ltd., Poole, England), pH 7.2 (PBS/Az), and subjected to surface immunofluorescence staining prior to analysis by flow cytometry. Approximately $0.5-1.0\times10^6$ cells were incubated with 100 µl hybridoma culture supernatant on ice for 30 mins. They were then washed twice in PBS/Az before incubation on ice for 30 mins with a 1/50 dilution of second antibody, fluorescein-conjugated affinity purified sheep anti-mouse immunoglobulin (SaMIg-FITC, Silenus, Dandenong, Victoria, Australia). After two further washes in PBS/Az, the cells were fixed prior to analysis using 1% paraformaldehyde (Sigma Chemical Company, St. Louis, Mo., U.S.A.) in PBS/Az (PF/PBS/Az). Flow cytometric analysis of immunofluorescent staining was carried out using a Fluorescence Activated Cell Sorter (FACS 440, Becton Dickinson, Mountain View, Calif.) equipped with a 5 W argon ion laser tuned to 488 nm at 200 mW.

b) Surface immunofluorescence staining of agarose embedded cells

Cells were assayed after embedding in agarose as described by Vartdal and co-workers (1986).

c) Immunohistology

BL-23 cells grown in chamber slides (Lab-tek Products, Miles Laboratories, Napierville, Ill.) or frozen sections from biopsy specimens were fixed for 5 min in acetone. The slides were washed in TBS for 10 min, biotinylated BLCA-8 (5 mg/ml) diluted 1/50 in PBS/Az was added and slides were then incubated for 1 h and washed 3 times in TBS. SA-HRP (Amersham, Sydney, NSW, Australia) diluted 1/200 in TBS was added to each slide, and after a further 1 h incubation, slides were again washed twice in TBS. Developing solution (3% $H_2O_2$ diluted 1/50 in 0.025% diaminobenzidine (Sigma)

in TBS) was applied and when the colour had appeared, slides were counterstained with Hematoxylin. All incubations were at 37° C.

Surface immunofluorescence results

The reactivity of BLCA-8, BLCA-30 and BLCA-38 was tested against short term cultures of normal bladder urothelium or urothelium from patients with TCC of the bladder, and against a series of human cancer lines from a variety of malignancies (Table 1).

A portion of normal bladder tissue was also obtained from a transplant donor. Cell suspensions were prepared mechanically from these tissues, and were stained for surface immunofluorescence, or after a period of up to 2 weeks in short term tissue culture. Cell lines were maintained as described above. The short-term cultures and cells from the bladder cancer cell line BL-13/0 were assayed by surface immunofluorescence of agarose embedded cells (see b) above) whereas all other human cancer cell lines were assayed by surface immunofluorescence and flow cytometry (see a) above).

Figure 1A:
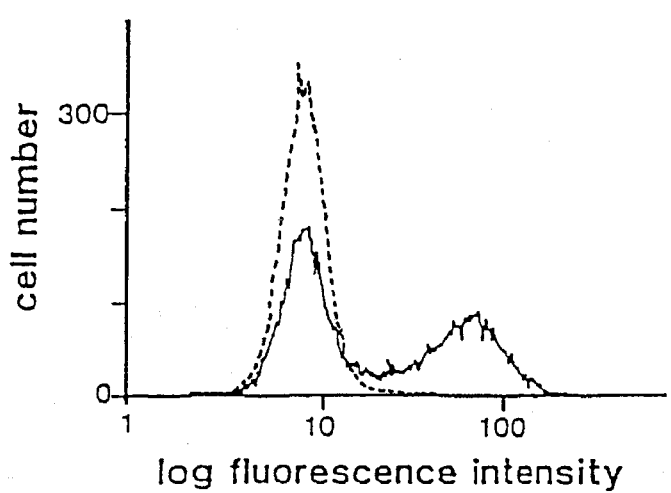
FIG. 1: Shows immunofluorescence profiles (solid lines) obtained by flow cytometric analysis of UCRU-BL-17-CL cells stained with BLCA-8 (A), BLCA-30 (B) or BLCA-38 (C) and SaMIg-FITC. The dotted lines indicate the profiles obtained with the control antibody and SaMIg-FITC.
Figure 1B:
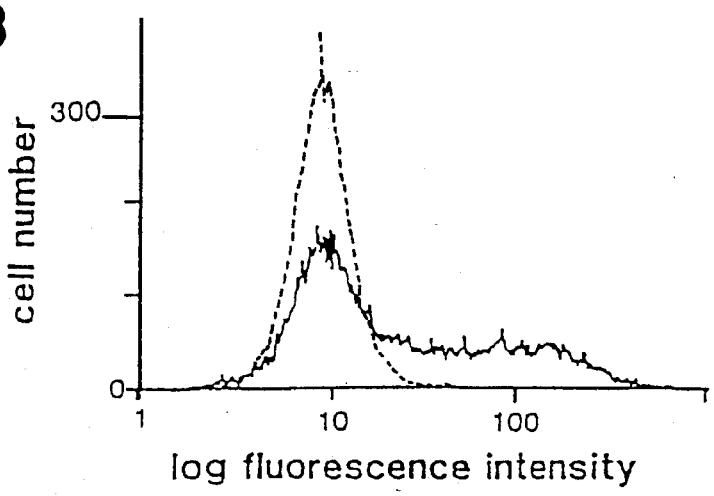
Figure 1C:
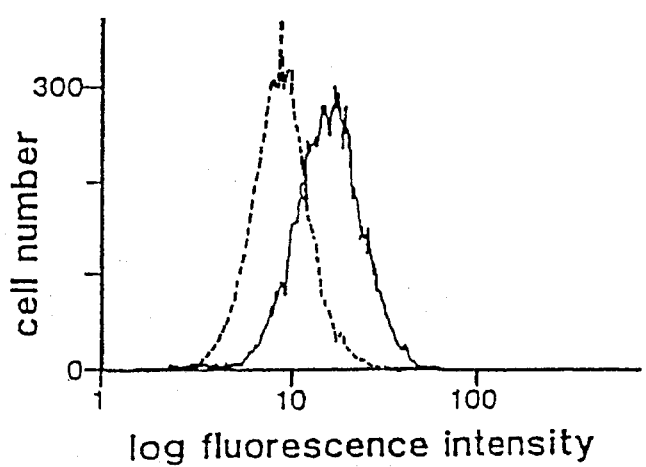

All three antibodies showed strong reactivity with BL-23 and BL-17 human bladder cancer cell lines (Table 1). An example of the flow cytometric profiles after staining of the BL-17 bladder cancer cell line is shown in FIG. 1.

The antibodies also reacted with short term cultures of TCC of the bladder, but did not react with normal bladder cells (Table 1). One MAb, BLCA-38, also showed reactivity with human ovarian and colonic cancer cell lines, and some melanoma lines. None of BLCA antibodies showed reactivity with lymphoid or leukaemic cell lines.

Immunohistological results

Figure 2A:
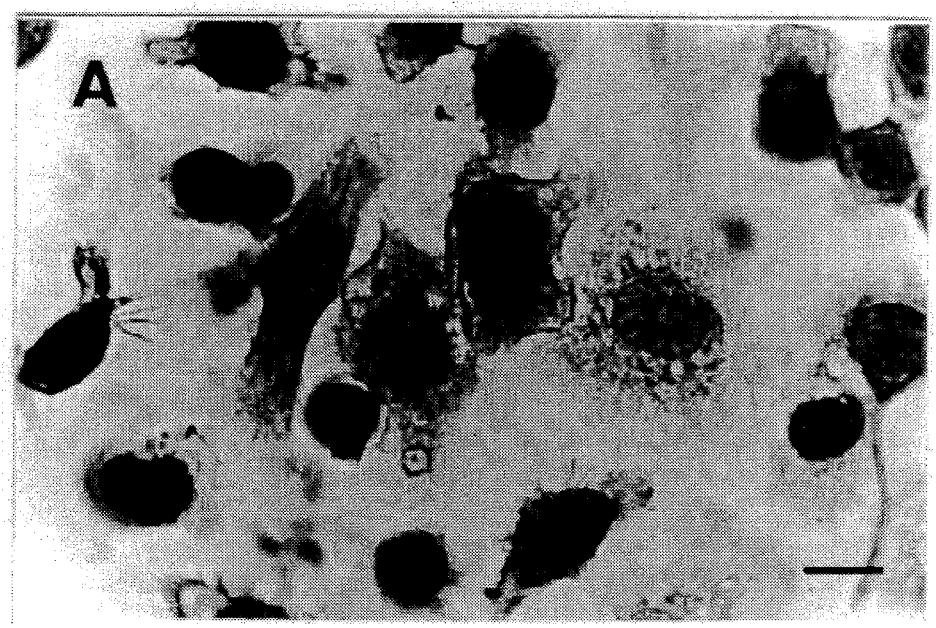
FIG. 2: Shows photomicrographs of BL-23 cells stained with A) biotinylated-BLCA-8 or B) biotinylated-K-1-21 (control) and SA-HRP. The bar indicates 10 μm.
Figure 2B:
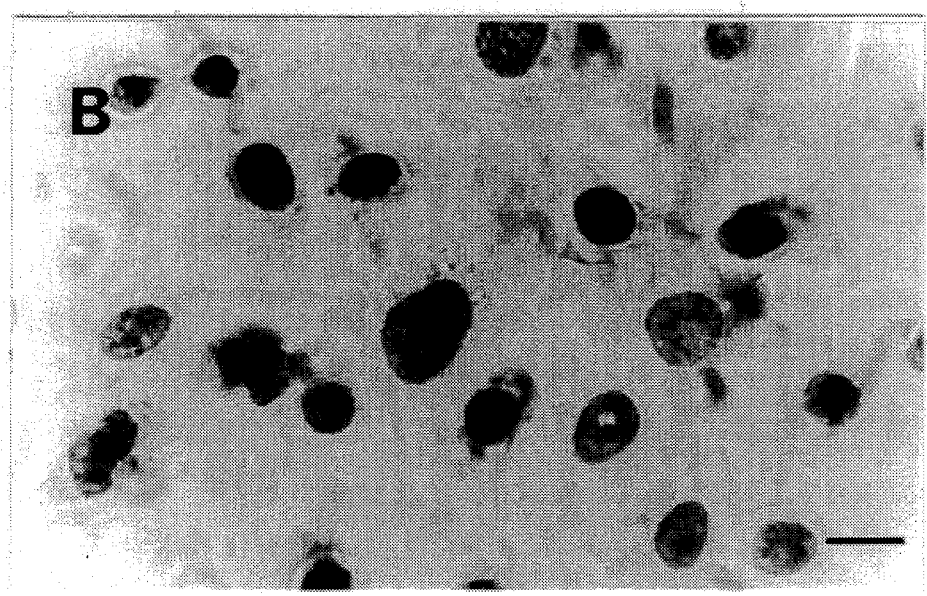

The BLCA-8 antigen was found to be poorly resistant to formalin fixation but was well preserved after treatment with acetone. Examples of BL-23 cells fixed in acetone and stained with biotinylated BLCA-8 and SA-HRP are shown in FIG. 2. Strong staining was observed both on the cell membrane and within the cytoplasm, whereas no cell membrane or cytoplasmic staining was observed with a control antibody. The reactivity of BLCA-8 with frozen sections from biopsy specimens from patients with TCC of the bladder, from patients with other malignancies, and from patients with non-malignant conditions of the bladder are shown in Table 2. BLCA-8 showed no reactivity with normal bladder, breast or testis. It was however, detected in sections of 17 week but not 14 week kidney and stomach. The BLCA-8 antigen may have some prognostic value. Positive reactivity was found in biopsy specimens from some patients with a previous history of TCC but with no known disease at the time of sampling. It was also found in some samples from patients with recurrent infection or haematuria but not in patients with chronic inflammation. BLCA-8 showed no reactivity with biopsy specimens from patients with benign conditions of the ovary or prostate but showed reactivity in ½ bladder conditions of benign origin. BLCA-8 reacted with all biopsy specimens from patients with TCC of the bladder (grades I–III) but showed no reactivity with breast or prostate adenocarcinoma.

EXAMPLE 3—Stability of antigen expression in cells exposed to urine

Figure 3:
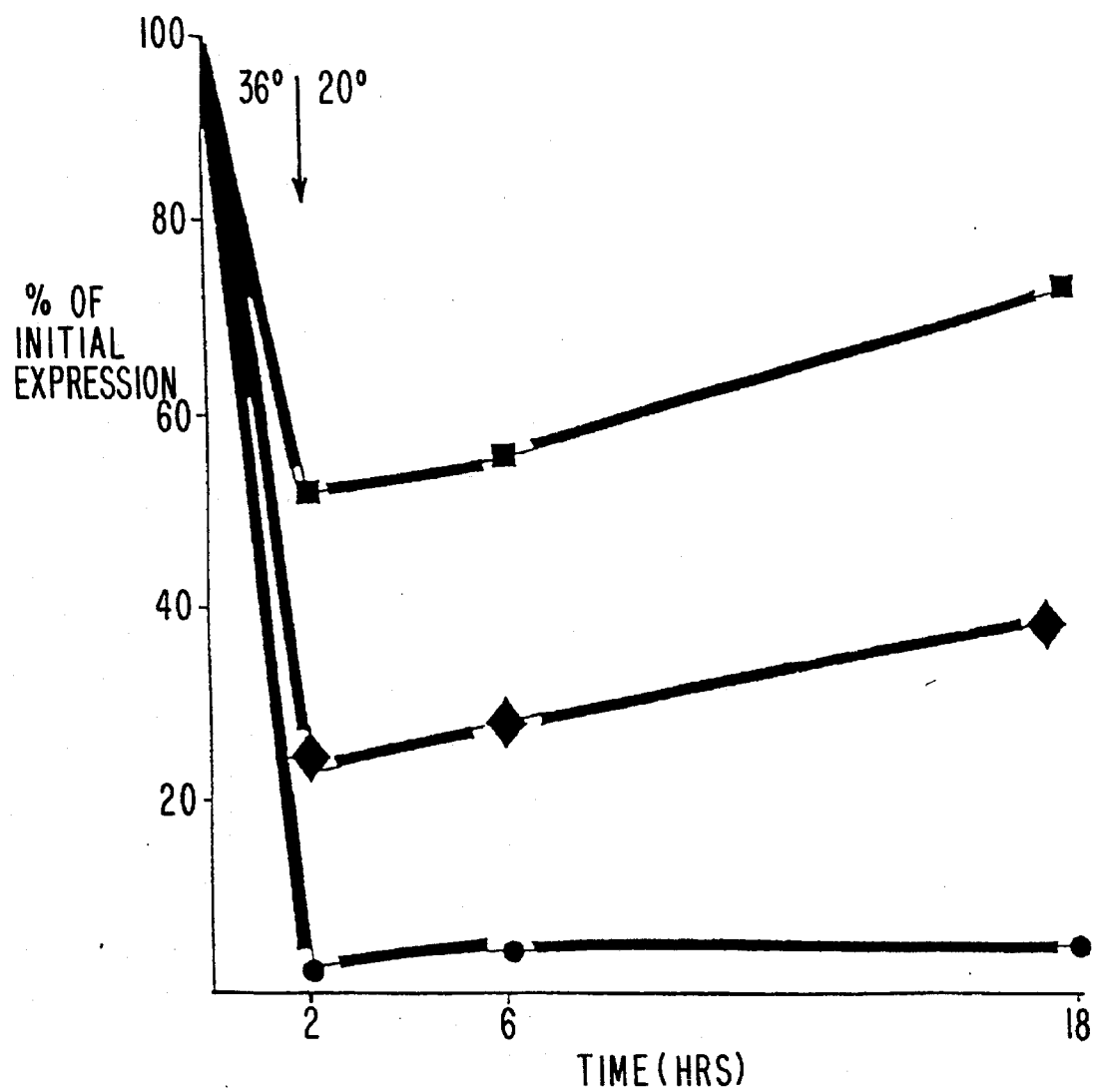
FIG. 3: Shows the effect of exposure to urine on antigen expression in UCRU-BL-17-CL cells. The cells were incubated in urine at 36° C. for 2 hours and then at 20° C. for a further 16 hours. At selected time points, the cells were stained with BLCA-8 ( ), BLCA-30 ( ) or with BLCA-38 ( ) followed by SaMIg-FITC.
Surface immunofluorescence was assessed by flow cytometry.

Cells of BL-17 were incubated in urine to determine the effect of exposure to urine on the expression of the BLCA antigens. Urine was centrifuged for 15 min at 2,500 rpm to remove debris. Ten million cells were incubated in 50 ml urine for 0, 2, 6 and 18 hours. The first two hours of each incubation were carried out at 36° C. to simulate body temperature; the rest of the incubation was carried out at room temperature. At the conclusion of each incubation, the urine was centrifuged for 10 min at 1,500 rpm. Cell viability was assessed by Trypan Blue exclusion, and $1 \times 10^6$ viable cells were subjected to standard surface immunofluorescence staining and flow cytometric analysis with each antibody as described above. The antigen detected by BLCA-8 proved to be the most stable after exposure to urine for 18 hours (FIG. 3), with 73% of the initial reactivity remaining at this time. In contrast, the antigen detected by BLCA-38 was almost completely lost.

EXAMPLE 4—Detection of malignant cells in voided urine

Twenty to fifty mls of urine were obtained from patients with biopsy-proven TCC of the bladder immediately prior to chemotherapy or surgery and from 10 normal controls (laboratory staff). The patients population sample consisted of 21 men aged 44–81 years and 3 women aged 67–75. The tumour stages included in this patient group were $T_{IS}$, $T_1$, $T_2$, $T_3$, and $T_4$ and the majority of tumours (22) were grade 3.

Exfoliated urothelial cells from the urine specimens of both controls and patients with cancer were assayed using an adaptation of the immunofluorescence method of Vartdal and co-workers (1986). Urine samples were centrifuged for 7 min at 1000 rpm and the cells were resuspended at $2 \times 10^5$ cells per ml in 100 µl of RPMI 1640 medium containing 40% FCS and mixed with an equal volume of molten 1% Sea Plaque agarose (SPA, FMC bioproducts, Rockland, Me., U.S.A.) in PBS. Two microliter aliquots of the cell/agarose mixture were placed on top of individual 15 µl aliquots of SPA (1% in PBS) precoated onto microscope slides. Supernatants (10 µl) from each hybridoma to be tested plus negative (K-1-21) controls were then placed over these individual aliquots of agarose-embedded cells. The slides were incubated in a humidified chamber at 4° C. for 30 min, before being washed in PBS/Az for 30 min at 4° C. Excess PBS was wiped from the slides, and 10 µl of second antibody, SaMIg-FITC diluted ⅟50, was added over each aliquot of agarose-embedded cells. After further incubation at 4° C. for 30 mins, the slides were again washed in PBS/Az before fixation in PF/PBS/Az. After mounting with 10% PBS-glycerol, immunofluorescent staining was assessed by fluorescence microscopy using a Zeiss photomicroscope.

Figure 4A:
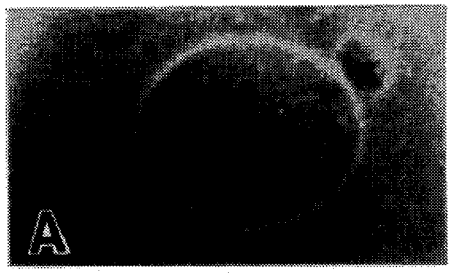
FIG. 4: Shows the appearance of inner layer (A and B) or outer layer (C and D) urothelial cells by either normal light microscopy (A and C) or after immunofluorescent staining with BLCA-8 and SaMIg-FITC (B and D).
Figure 4B:
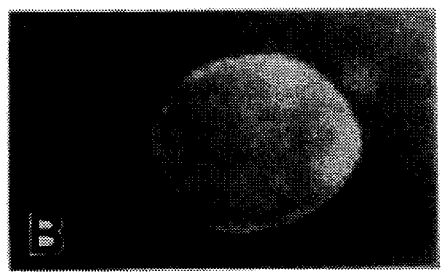
Figure 4C:
Figure 4D:
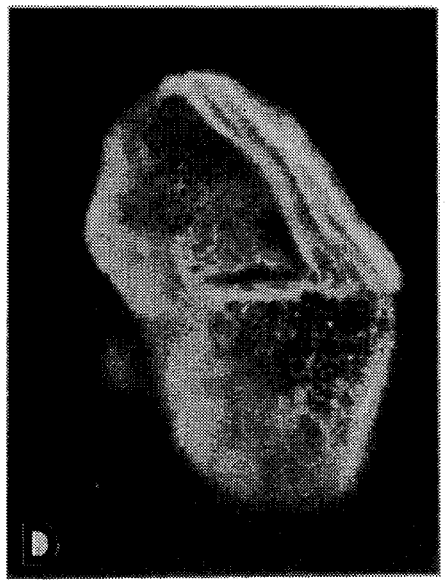

Counts were made of two cell types; the large, irregular cells from the outer layer of the urothelium ("outer cells") (FIG. 4c and d) and the smaller rounder cells of the inner layers ("inner cells") (FIG. 4a and b) as described by Piccoli and co-workers 1984. Normally 100 cells of each type (a minimum of 50) were assessed for fluorescence with each MAb tested and the percentage of positive cells was recorded.

No reactivity was detected with the negative control antibody.

Figure 5A:
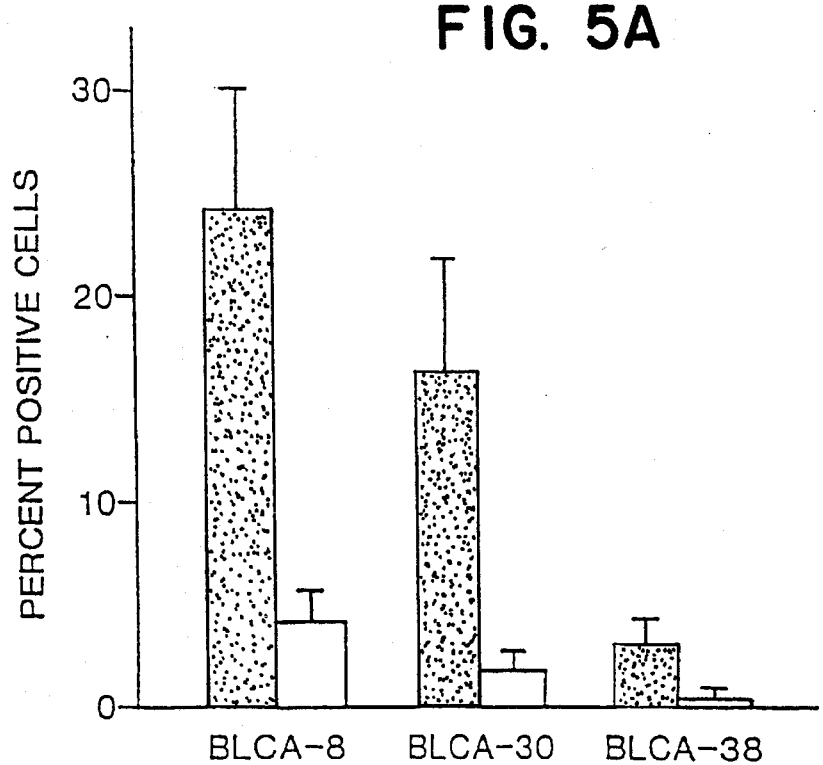
FIG. 5: Shows reactivity of agarose-embedded cells from voided urine samples of patients with TCC of the bladder (solid histograms) or normal controls (open histograms). Cells were stained with BLCA-8, BLCA-30 or BLCA-38, followed by SaMIg-FITC. Reactivity was assessed by fluorescence microscopy. A) Inner layer cells, B) Outer layer cells. Vertical bars indicate the standard error of the mean.
Figure 5B:
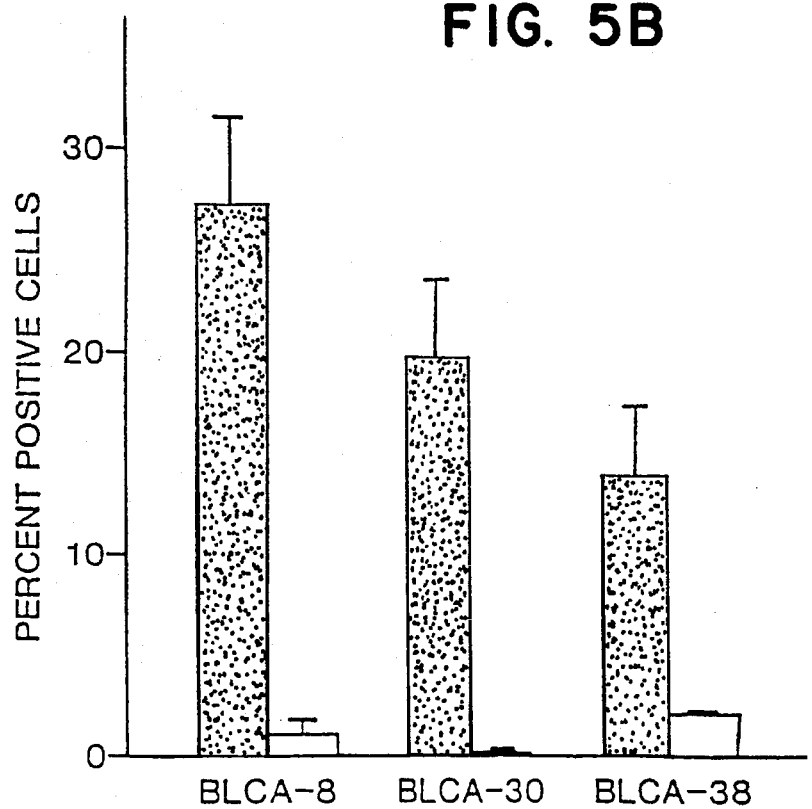

The percentages of cells showing reactivity with BLCA-8, –30 and –38 in urine samples from cancer patients and in controls are shown in FIG. 5. Each MAb showed a significantly higher reactivity against patients' cells than against normal control urothelial cells. The greatest difference was observed with BLCA-8 where the percentages of positive cells in patients' urine were 24.3, ±5.8 and 27.0±4.6 for outer and inner layers, respectively, as compared with 2.9±1.0 percent and 0.8±0.5 percent in cells from control urines ($P<0.05$ and $P<0.002$, respectively). Positively staining cells in patients' urine were also readily apparent with BLCA-30. BLCA-38 showed a higher positive staining on inner, but not outer layer urothelial cells, as compared with cells from normal controls.

EXAMPLE 5—Comparison of the detection of malignant cells in voided urine by the agarose assay with their detection by conventional cytology Urothelial cells from 8 patients with biopsy proven TCC of the bladder included in the population sample described in Example 3 were examined by cytology and the results were compared with those obtained by the agarose assay (Table 3). The urine samples were cytocentrifuged, air-dried and then fixed in cold 95% ethanol before staining with a modified Papanicolou stain. The specimens were analysed for morphology by an experienced cytopathologist. By standard cytology 4/8 patients with biopsy-proven TCC had urothelial cells in the voided urine which were considered positive for malignancy (Table 3). In 2/8 patients atypical cells were observed and the samples were thus deemed "suspicious". In 2/8 patients the results were negative. In contrast in the MAb agarose assay 5/8, 7/8 and 6/8 samples showed positive reactivity with BLCA-8, BLCA-30 and BLCA-38 respectively.

With the exception of patients 2 and 8 who were clinically in remission at the time when urine samples were taken, all of the biopsies were carried out within two days of urine sampling. The results obtained therefore related to the current clinical status of the patients.

EXAMPLE 6—Relation between the expression of the BLCA-8 reactive antigen on cells in voided urine and the stage of invasiveness of the tumour The patient population sample described in Example 3 was increased by the addition of 8 further patients. The sample now consisted of 28 men aged 44–81 and 4 women aged 48–75. The tumour stages represented in this patient group were as follows (patient numbers are given in brackets): $T_{is}$ (carcinoma in situ) (1) $T_1$ (invasion of the lamina propria (2); $T_2$ (superficial muscle invasion) (9); $T_3$ (deep muscle invasion) (14); $T_4$ (invasion of surrounding organs) (6). Two patients (one $T_3$ and one $T_4$) were thought to be in remission. Two tumours were grade II while 30 were grade III.

A further 8 normal controls were also added to the control sample described in Example 3. This group now included 11 men aged 21–51 and 7 women aged 21–59. It also included 3 pregnant women, 3 heavy smokers, one case of urinary tract infection and one patient with a urethral stricture. Other cases of interest are described in Table 4.

Figure 6:
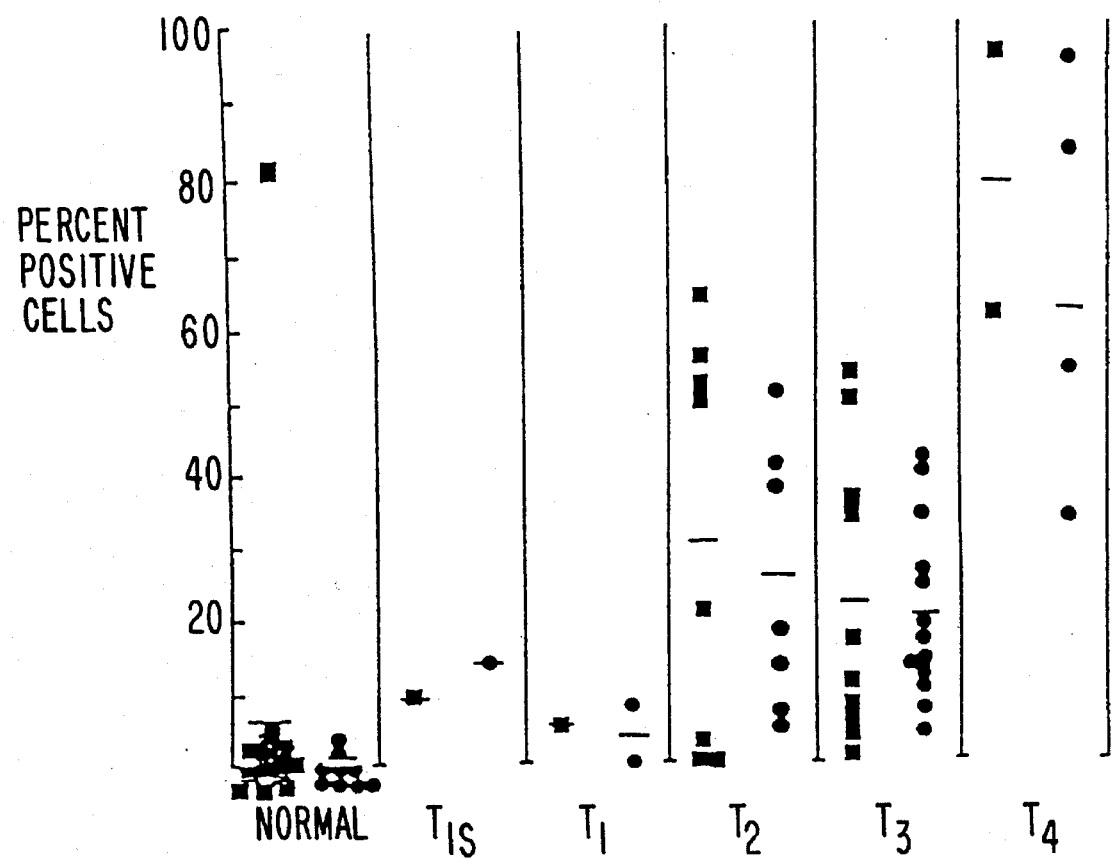
FIG. 6: Shows the percentage of outer ( ) and inner ( ) urothelial cells from voided urine reactive by surface immunofluorescence in an agarose assay with BLCA-8. Samples were obtained from normal controls and from patients with biopsy-proven TCC of the bladder.
The horizontal bar indicates the arithmetic mean in each group. Each point is taken from a count of at least 50 cells.

Agarose-embedded cells obtained from voided urine from these patients or normal controls were stained with MAbs as described in Example 3. The results of this study are shown in FIG. 6. Urothelial cells from patients with TCC showed marked reactivity with BLCA-8 (30.4±5.8% outer and 28.9±4.4% inner cells positive) and expression of the BLCA 8 antigen appeared to increase with tumour stage. For $T_4$ tumours, where invasion of surrounding organs has occurred, means BLCA-8 reactivity was 79.0% for outer and 62.5±10.7% for inner cells. This was significantly higher than figures obtained from normal controls (6.06±4.71% outer and 0.6%±0.4% inner cells positive, $P<0.02$ and $P<0.001$ respectively, Student's t-test). The increased expression of the BLCA-8 antigen on tumours of higher stage may be the result of either an increase in the numbers of malignant cells shed into the urine or it may indicate an interesting new marker of neoplastic invasion.

In the normal population, BLCA-8 expression on urothelial cells was minimal except in the case of one person, a female, heavy smoker aged 50, who was found on two separate occasions to have a high reactivity with BLCA-8 (78–81% outer cells positive) (FIG. 5 and Table 4). Examination of these cells by an experienced cytopathologist, revealed the presence of "atypical" cells in her voided urine, but cytoscopy revealed no evidence of malignancy. BLCA-8 expression remained low in 2 other subjects who were also heavy smokers (2 cases) and also in 3 women who were pregnant. Other cases of interest examined are shown in Table 4. Urothelial cells were examined from two patients who had undergone cystectomy but no BLCA-8 reactivity was detected. Two patients with a prior history of TCC ($T_3$ tumours) but no evidence of malignancy at the time of urine sampling, were also examined. One had 67% outer cells positive while the other had 72% outer and 20% inner cells positive. The first patient developed carcinoma in situ four months after sampling; the second was found to have a papillary tumour, grade I–II, five months later. Finally, one patient with a degenerating cyst in the kidney showed 14% cells positive with BLCA-8 while another patient with pyuria of unknown origin also had 14% cells positive.

EXAMPLE 7—Expression of the BLCA-8 antigen in the cytoplasm

Figure 7A:
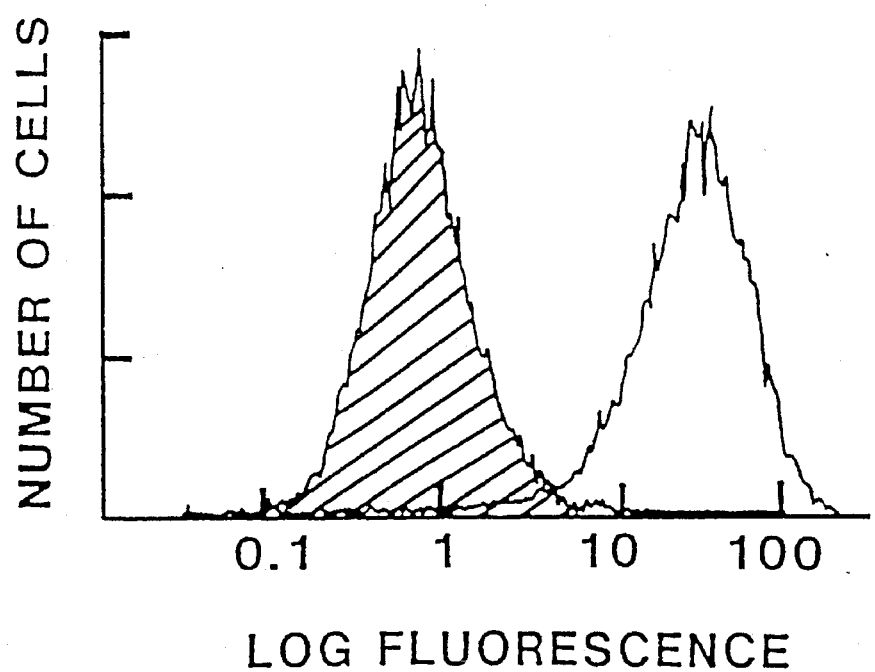
FIG. 7: Shows immunofluorescence profiles obtained after flow cytometric analysis of BL-23 cells stained with BLCA-8 (clear histogram) or K-1-21 (control, shaded histogram) and SaMIg-FITC. A) Surface immunofluorescence B) Cytoplasmic immunofluorescence. Ten thousand cells were analysed in each sample.
Figure 7B:
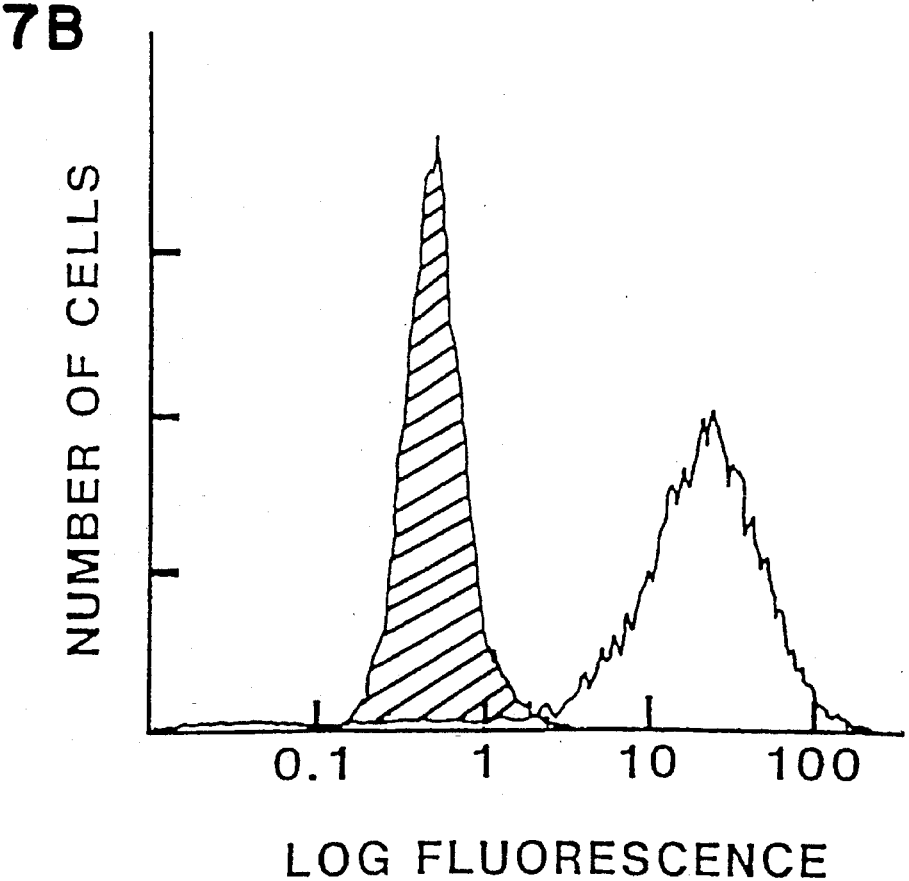

The cytoplasmic expression of the BLCA-8 antigen on BL-23 cells was determined by fixation of the cells in 50% ethanol/PBS at 4° C. for 5 min and immunofluorescence staining with BLCA-8 and SaMIg-FITC followed by flow cytometric analysis. When the results were compared with surface staining (as described in Example 2, method (a)) it was found that 94% of BL-23/3 cells had positive staining for BLCA-8 and 80% also showed positive cytoplasmic staining (FIG. 7). The BLCA-8 antigen is thus expressed both on the cell surface and in the cytoplasm.

EXAMPLE 8—Characterisation of the BLCA-8 Antigen a) Effects of enzymatic and chemical treatments on the cell surface expression of BLCA-8 antigen Studies were undertaken to characterise the nature of the BLCA-8 antigen by modification of the cell surface by a number of chemical and enzymatic treatments (Zola et al. 1984, a, b) (Table 5).

BL-17 or BL-23 human bladder cancer cells were harvested with EDTA as above, washed once with PBS and treated with (a) pronase (protease Type XIV, Sigma, St. Louis, Mo.) 0.5 mg/ml, $5\times10^6$ cells in 1 ml PBS for 1 h; (b) neuraminidase (*Clostridium perfrigens*), (Sigma) 0.1 U/ml, $1\times10^7$ cells in 0.05M sodium acetate buffer, pH 5.5, with 1% $CaCl_2$ for 45 min; (c) ECTA, 0.1M $5\times10^6$ cells in 1 ml PBS for 1 h; (d) 2-ME (Sigma), $5\times10^6$ cells in 1 ml PBS for 1 h at 4° C.; (e) fucosidase (bovine epididymus, Sigma) 0.031 U/ml, $1\times10^6$ cells in 500 µl PBS for 30 min (f) sodium periodate (Sigma) 1 mM, $5\times10^6$ cells in 1 ml PBS for 1 h at 4° C. In addition, cells were incubated with *Limulus polyphemus* lectin (Sigma), 500 µg/ml, $1\times10^6$ cells in 500 µl PBS, 0.1 mM $CaCl_2$ for 30 min. Incubations were at 37° C. unless otherwise stated. Following these treatments, the cells were washed in PBS and 1×10⁶ viable cells were subject to immunofluorescent staining and flow cytometric analysis (as above).

Expression of the BLCA-8 antigen was unaffected by pronase or endoglycosidase F (Table 5) which suggests that the antigen is unlikely to be protein or glycoprotein in nature. Moreover, surface expression of the antigen does not appear to be dependent on divalent cation bridges or disulfide bonds since EDTA or 2-ME had no effect on antigen expression. In addition, the epitope does not appear to involve sialic acid since treatment of the cell surface with mild periodate oxidation or with neuraminidase to cleave sialic acid groups did not affect antibody binding. Neither was binding blocked by Limulus lectin which has specificity for sialic acid residues.

b) Heat stability of the BLCA-8 antigen

The BLCA-8 antigen can be detected in spent medium from BL-23/3 bladder cancer cells by ELISA. This assay was used to determine whether the BLCA-8 antigen was stable to heat treatment.

Spent medium was obtained from confluent cultures of BL-23 cells overgrown for 7 days in 25 cm² tissue culture flasks (Costar, Delta Packaging, Cambridge, Mass.). Duplicate 400 µl aliquots of spent medium, were serially diluted in PBS in the wells of a 96 well plate (Flow Laboratories Inc., McLean Va.). After O/N incubation, wells were washed in PBS and blocked with 2.5% BSA (Miles Diagnostics, Sydney, Australia) in PBS for 1 h. The wells were again washed in PBS before 100 µl of BLCA-8 SN was added. Plates were incubated for 2 h, then washed in PBS before addition of SaMIg-B (Sigma), 100 µl/well diluted 1/500 in 1% BSA-PBS. After a further 2 hr incubation and PBS wash, A-AP (Sigma) (100 µl/well diluted 1/500 in PBS) was added. Plates were incubated and washed as before.

Figure 8:
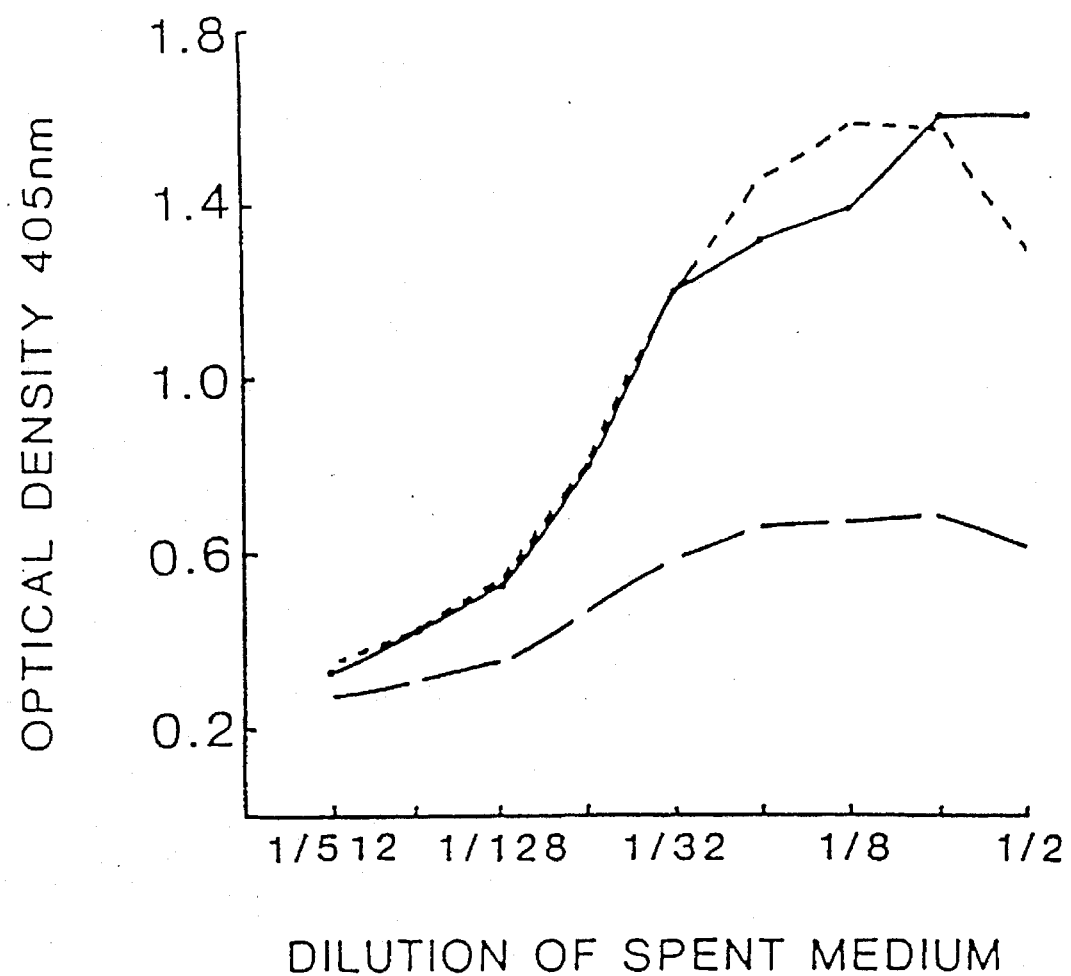
FIG. 8: Shows binding of BLCA-8 by ELISA to antigen present in spent media from BL-23 cells ( ), in spent media after boiling ( ), and in normal culture media ( ) (control).

Enzyme substrate was then added. All incubations were at 37° C. The results of these treatments are shown in FIG. 8. The BLCA-8 antigen appeared to be stable after treatment at 100° C. for 90 seconds and was detectable in UCRU-BL-23/3 spent medium at dilutions of less than 1/128.

c) Expression of the BLCA-8 antigen in lipid extracts from human bladder cancer cells The resistance of the BLCA-8 antigen to pronase and endoglycosidase F treatment (Table 5) and its heat stability (FIG. 8), suggest that it is lipidic in nature. This was confirmed by the reactivity of BLCA-8 with lipid extracts prepared from both the BL-17 and the BL-23/3 bladder cancer cells lines.

Lipid extraction from BL-17 or BL-23 cells was carried out as described by Magnani and co-workers (1981). A lipid extract from BL-17 cells was further purified as follows. The extract was dissolved at 10 mg/ml in chloroform:methanol, 1:1 (v/v) and purified by preparative TLC on silica gel 60 F0254 plates (Merck, Darmstadt, FRG) using chloroform:methanol:water, 60:35:8 (v/v) as solvent. Standards of $G_{m1}$, $G_{M1}$, $G_{D1a}$ and $G_{M3}$ gangliosides (Sigma) (nomenclature follows Svennerholm (1964)) were run on each side of the plate and later stained with anthrone (as below). Glycolipidic bands with chromatographic mobility related to those of the standard gangliosides were located under UV light, scraped from the plate and then extracted by 80 ml of chloroform:methanol (1:1) before drying.

The two lipid extracts were examined for the presence of the BLCA-8 antigen by ELISA. Extracts were solubilized in absolute ethanol at 20 µg/ml (BL-17 extract) or 2 µg/ml (BL-23 extract) and serially diluted in the wells of a 96 well plate (Flow). Fifty 82 l were added per well with 4 replicates at each dilution.

Gangliosides $G_{m1}$ and $G_{D1a}$ were used as controls.

Wells were evaporated to dryness, the plate was washed once in PBS and wells were then blocked with 2.5% BSA in PBS and incubated O/N at 4° C. The plate was washed 4 times in PBS before addition of BLCA-8 SN (test) or BLCA-7 SN (a control MAb reactive to blood group A). (100 µl/well). The plate was then incubated for 2 h at 37° C. and washed 3 times in PBS and once with 1% BSA in PBS. SaMIg-B, A-AP and enzyme substrate were then added.

Figure 9A:
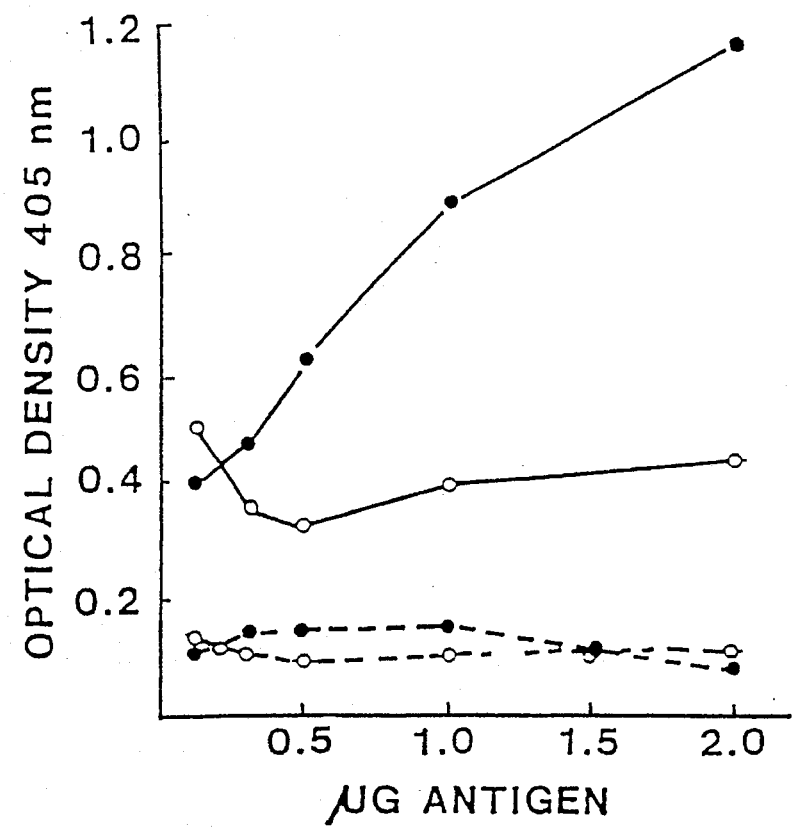
FIG. 9A.
Figure 9B:
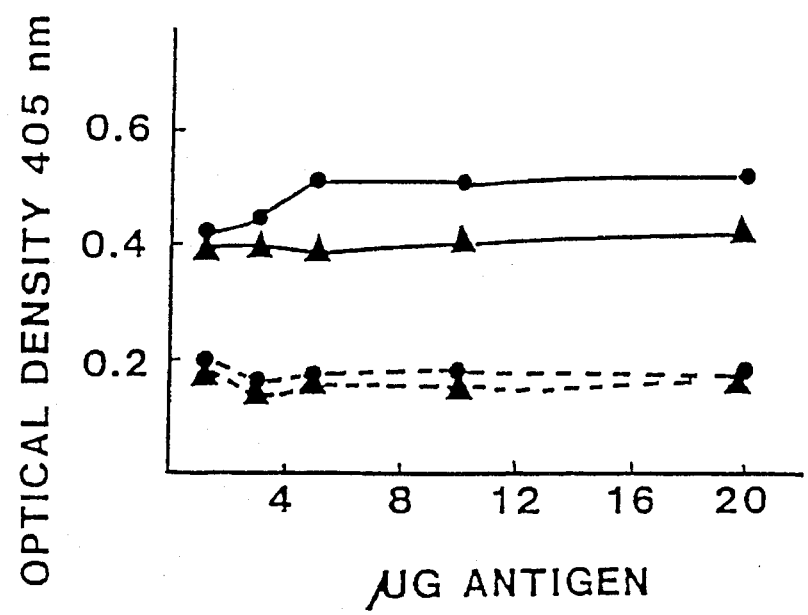
FIG. 9B: Shows the binding of these same test and control MAbs against a lipid extract prepared from BL-17 cells ( ) or against ganglioside G$_{m1}$ ( )

In the ELISA, BLCA-8 showed good reactivity with lipid extracts from both BL-23/3 (FIG. 9A) and BL-17 (FIG. 9B) although clearly more antigen was present in the BL-23 extract. No reactivity with either BL-17 or BL-23 lipid extracts or the standard gangliosides was observed with a control antibody of matched IgG₃ isotype.

d) BLCA-8 reactivity with Lewis blood group antigens

The BLCA-8 reactive bladder cancer cell lines were known to also react by surface (immunofluorescence with BG-8 (anti-Le$^y$) and BG-5, (anti-Le$^a$) MAbs (Cambridge Research Laboratories, Cambridge, Mass.). BL-17 cells were also reactive with BG-6 (anti-Le$^b$) and BG-7 (anti-Le$^x$) (Cambridge Research Laboratories). The anti-Lewis antibodies were kindly provided by Dr. L Old, Memorial Institute, Sloan Kettering, N.Y. BLCA-8 was therefore tested for reactivity with a panel of Lewis positive human RBC by three standard serological techniques. These tests were kindly carried out by the N.S.W. Red Cross Transfusion Service, Sydney, through the auspices of Mrs A. Fletcher. A panel of Lewis a⁺, b⁺ and c⁺ positive human RBC were used.

In addition BLCA-8, BLCA-30 and BLCA-38 all fail to cross-react with group A human red blood cells either by surface immunofluorescence staining or by serology.

e) Effect of enzymatic and chemical treatment of lipid extracts on BLCA-8 binding in an ELISA A BL-23 lipid extract, prepared as above, was subjected to various enzymatic or chemical treatments before BLCA-8 binding in an ELISA in order to further characterise the BLCA-8 antigen. The extract was dissolved in absolute ethanol and 60 µl of a 10 µg/ml solution was added to the wells of a 96 well plate (Flow) and evaporated to dryness. Wells were then blocked with 2.5% BSA in PBS with 1 mM CaCl₂ for 2 h before incubation at 37° C. with sodium periodate (Sigma) at 1.0 to 100 mM for 1–2 h or with various enzymes diluted in PBS/CaCl₂ at the following concentrations:

α-galactosidase, 240 µl at 0.5 U/ml for 2 h or 350 µl at 0.7 U/ml O/N; β-galactosidase, 200 µl at 25 U/ml O/N; α-glucosidase, 350 µl at 2.5 U/ml O/N; β-glucosidase, 350 µl at 0.055 U/ml O/N. Control wells received PBS/CaCl₂ alone. After incubation, plates were washed 4 times in PBS/CaCl₂ and 100 µl of BLCA-8 SN were added in duplicate to enzyme-treated and non-treated wells. Remaining wells received PBS/CaCl₂ only. Plates were then incubated for 2 h and washed as above. BLCA-8 treated wells received SAMIg-B (Sigma) (100 µl/well of a 1/500 dilution) Other wells received 100 µl of a 1/500 dilution of biotinylated lectin solution. Biotinylated lectins (E-Y Laboratories, San Mateo, Calif.) were used as indicators of enzyme activity. This activity of α- and β-galactosidase was confirmed with GS-I, which binds α-gal and β-galNac end groups; DBA, which binds terminal non-reducing α-D-N-acetylgalactosamine; and SBA, which recognises terminal non-reducing N-acetylgalactosamine (α>β). Activity of α- and β-glucosidase was confirmed with WGA, which binds N-acetyl-glucosamine (β-linked trisaccharide>monosaccharide) and with Con A which binds α-mannose, α-glucose and α-N-acetylglucosamine. Activity of α-fucosidase was confirmed with UEA-I, which recognises α-L-fucose. Con A was used at a dilution of 1/1250 from a 2.5 mg/ml solution in TBS/CaCl$_2$ while all other lectins were used at a dilution of 1/500 from a 1 mg/ml solution in PBS/CaCl$_2$. After incubation with biotinylated reagents for 1 h, plates were washed as above before addition of a 1/500 dilution of A-AP in PBS/CaCl$_2$ to each well.

Incubation of a lipid extract of BL-23 cells with up to 100 mM sodium periodate was found to have no effect on BLCA-8 binding (Table 6). This periodate resistance would indicate that if carbohydrate moieties are recognised by BLCA-8 they may be modified by O-acyl, O-methyl or O-acetyl groups or may be linked at position 3.

Further studies also examined the effect of treatment with various enzymes. In each case the activity of each enzyme used was verified by changes in the binding of appropriate biotinylated lectins (data not shown). While most enzyme treatments had no effect, overnight incubation of the lipid extract with β-galactosidase or with α-glucosidase was found to cause a marked increase in BLCA-8 binding (Table 6). This suggests that the expression on the BLCA-8 antigen may be partially masked by β-galactose and α-glucose residues. Glycolipids are known to act as "cryptic" components of the membrane whose interaction with external ligands can in turn be regulated by "masking" factors which are part of the cell membrane machinery controlling membrane function (Sonnino 1988).

f) Immunoblotting BLCA-8 Antigen in Lipid Extracts

Purified BL-17 extracts were solubilized at 1 mg/ml in chloroform:methanol, 1:1 and applied as 1, 2, 3 µg spots to 3 replicate K6 silica gel TLC plates (Whatman, Alltech Associates, Deerfield, Ill.) as described by Ridell and co-workers (1986). Plates were developed in chloroform:methanol:water as above. One plate was then stained with anthrone (as below) while the other two were immunoblotted with BLCA-8 (test) or K-1-21 (control) SNs and $^{125}$I-SaMIg following methods described by Magnani and co-workers (1981). X-ray film (XRP-1 Kodak Australasia, Sydney) was then exposed to the air-dried plates using cassettes with intensifying screens (X-omatic, Kodak).

BL-23 extracts were solubilized at 10 mg/ml in 1:1 chloroform:methanol and 60 or 90 µg was applied to 6 replicate TLC plates. Ganglioside G$_{D1}$ (1 µg) was applied as a standard. Plates were run as above. Four plates were visualised with TLC spray reagents (see below) while the 2 remaining plates were immunoblotted (as above) with BLCA-8.

Both BL-17 and BL-23 lipid extracts were separated by TLC before immunoblotting with BLCA-8 (test) or K-1-21 (control) SN and $^{125}$I-SaMIg. BLCA-8 was found to bind specifically to three components (2 major and 1 minor) in the BL-17 extract while no staining occurred with the control MAb (data not shown). BLCA-8 also bound to 4 components (2 major and 2 minor) in the BL-23 extract which had a pattern of migration approximating those components specifically stained in the BL-17 extract (FIG. 10A). Again no specific staining was observed with the control antibody (FIG. 10B).

The differences between major and minor components reactive with BLCA-8 in these lipid extracts remain to be characterized but they represent related lipids which differ in glycosylation. Abnormal glycosylation of cellular antigens has been commonly described in various tumours (Hakomori et al. 1984) including the BL-17 bladder cancer xenografts and cell lines (Russell et al. 1988).

One TLC plate to which the BL-17 extract had been applied was stained with anthrone. The 12 glycolipids detected in the extract included 3 components which had been found to react with BLCA-8 by immunoblotting (FIG. 10). Similarly, 13 glycolipids were detected in the BL-23 extract by reaction with orcinol (Table 7) and these again included the BLCA-8 reactive components detected by immunoblotting.

Further staining of the components in the two bladder cancer cell lipid extracts was carried out after thin layer chromatography to determine the nature of the BLCA-8 reactive components identified by immunoblotting (Table 7). The BLCA-8 reactive components were not visualised with resorcinol and thus did not appear to be gangliosides or to contain sialic acid. The BL-23 extract was found to contain several phospholipids after staining with Molybdenum Blue (1.3% molybdenum oxide in 4.2M sulphuric acid) but these did not include the BLCA-8 reactive components. Thus by exclusion, the BLCA-8 reactive moieties are either neutral glycolipids or sulphatides which stain with α-napthol (Table 7).

g) Separation of BL-23 lipid extract into acidic lipid and neutral lipid fractions Two grams of BL-23 cells were extracted for lipid as described by Magnani and co-workers (1981). The pooled extract was made up to a final volume of 200 ml in methanol:chloroform:water 60:30:8. The extract was then applied to a column of DEAE-Sephadex-25 as described by Ledeen and Yu (1982) to separate the extract into acidic lipid and neutral lipid fractions. Aliquots of both lipid fractions were then serially diluted and added to the wells of a 96 wells plate for an ELISA with BLCA-8 as described in Example 8 (c). BLCA-8 reactivity was present in the neutral glycolipid fraction.

EXAMPLE 9—Localisation of radiolabelled BLCA-38 to human bladder cells cancer xenografts in nude mice

Animals

Athymic BALB/c nu/nu ("nude") mice were bred at the Australian Nuclear Science and Technology Organisation (ANSTO) laboratories at Lucas Heights, NSW, Australia and at approximately six weeks were transferred to the Nude Mouse Facility, Blackburn Building, University of Sydney. The mice were kept under sterile conditions, being housed in cages fitted with filter tops, and were fed sterilized standard mouse found and water ad libitum.

When radioiodinated antibodies were to be injected, the animals' drinking water was supplemented with potassium iodide (0.05%) to block uptake of the radioiodine by the thyroid gland.

Xenografts

Human bladder cancer xenografts derived from the BL-17 line were maintained in serial passage as described previously (Russell et al. 1986).

Murine Monoclonal Antibodies

Antibodies were concentrated to 1 mg/ml for iodination and to approximately 20 mg/ml for chelation with $^{153}$Sm or $^{111}$In and were stored at −20° C.

Radiolabelling of Proteins

Antibodies were labelled with $^{131}$I as described previously (Walker et al. 1986). $^{111}$In (Amersham, Bucks, UK) or $^{153}$Sm (Australia Nuclear Scientific and Technology Organisation, ANSTO, Lucas Heights, NSW, Australia) were chelated to antibodies using the bicyclic anhydride of diethylenetriaminepentaacetic acid (DTPA) as a bifunctional chelating agent using methods developed by Boniface and co-workers (1989). Briefly, the bicyclic anhydride of DTPA (Sigma, St. Louis, Mich.) at 1 mg/ml in chloroform was dried under nitrogen onto the sides of an acid washed Reactivial (Pierce Chemical Co., Rockford, Ill.). Antibody (20 mg/ml) was added at a ratio of 20:1 (DTPA:Ig). The vial was then vortexed for 1 min and left at room temperature for a further 20 min. Free DTPA was removed by passage over Sephadex G-50 (Pharmacia, Uppsala, Sweden). Isotope ($^{111}$In-acetate or $^{153}$Sm-chloride) was added to the DTPA-Mab conjugate and the solution was left at room temperature for 30 min before removal of free radionuclide by passage over Biogel P-6DG (Biorad, Richmond, Calif.).

Stability of $^{153}$Sm-BLCA-38 Conjugates

The stability of $^{153}$Sm-BLCA-38 conjugates was investigated in a study carried out by Dr. G. Boniface, Australian Nuclear Science and Technology Organisation, Sydney. Mouse plasma was obtained from heparinised pooled blood samples taken from normal BALB/c mice and spun at 800 g for 10 min. $^{153}$Sm-BLCA-38 was spiked into the plasma and incubated at 37° C. for 48 h. Aliquots were taken at 0, 3, 24, 48 h, filtered through a 0.02 micrometer anatope filter (Anotec Separations Limited, Oxon, UK) which was subsequently counted (as below) for radioactivity. The filtrate was then analysed by quantitative size exclusion HPLC (Biosil TSK 250, 7.5×300 mm, 0.2M Tris buffer pH 7.0). Column elution was monitored with an in line 280 nm UV detector and gamma spectrometer. Retention times were compared with those obtained with protein standards and unlabelled BLCA-38 MAb.

Imaging and Biodistribution Studies

Groups of 5–6 nude mice were implanted subcutaneously on each flank with a BL-17 human bladder cancer xenograft. Three weeks later, when tumours were approximately 200–1,000 mm$^3$, the mice were injected with $^{131}$I-, $^{111}$In- or $^{153}$Sm-labelled BLCA-38 or a labelled control MAb. In addition, one group of normal nude mice without BL-17 xenografts were injected with $^{153}$Sm-BLCA-38. Each mouse received 80–120 μg of protein labelled with 300–500 μCi of isotope.

Seven days after injection of $^{131}$I-BLCA-38 or $^{131}$I-control MAb, mice were anaesthetised and placed prone beneath the pinhole collimator of a large field of view (LFOV) Searle Pho Gamma IV gamma camera (Searle, Des Plaines, Ill., USA).

Images were taken using a 25% window centred at the 360 KeV peak for $^{131}$I. Each image was collected for 5 mins and was stored by an on line computer (Digital PDP 11/23 plus) on a 64×64 matrix. Images were photographed from the visual display unit after interpolation to a 128×128 matrix.

Seven days after injection of $^{111}$In- or $^{153}$Sm-labelled MAbs, and when imaging was completed for mice injected with $^{131}$I-labelled MAbs, anaesthetised mice were exsanguinated by cardiac puncture and killed by cervical dislocation. Tissues and xenografts were dissected, weighed and counted using a 1274 Riagamma gamma counter (LKB Wallac, Stockholm, Sweden) tuned to 360 KeV, 170–250 KeV, or 103 KeV for the gamma emissions of $^{131}$I, $^{111}$In, or $^{153}$Sm respectively. In order to determine whether deposition of $^{153}$Sm in bone was associated with osseous bone or with bone marrow, marrow was expelled from the long bones with saline after counting and the bones were then reweighed and recounted.

Tissue distribution profiles of percent injected dose/g (% ID/g) and tissue:blood (T:B) ratios were generated using a computer biodistributor programme. Data were compared by Student's t-test.

Results a) Radioimmunoscintigraphy with Iodinated MAbs

Scintigraphic images were taken of nude mice bearing BL-17 human bladder cancer xenografts, seven days after injection of $^{131}$I-BLCA-38 or $^{131}$I-L7 control MAb (FIG. 11). The $^{131}$I-BLCA-38 localised to the xenografts yielding images in which the tumour sites were clearly discernable whereas the control antibody remained in the circulating blood pool giving no tumour definition.

b) Biodistribution Studies

Biodistribution studies were carried out on nude mice bearing s.c. BL-17 human bladder cancer xenografts, seven days after injection of $^{131}$I-, $^{111}$In- or $^{153}$Sm-BLCA-38 or $^{131}$I-L7 or $^{111}$In- and $^{153}$Sm-control MAbs.

Tissue uptake as percent injected dose per gram (% ID/g) is given in Table 8. The radioactivity deposited in the BL-17 xenograft was greatest after injection of the $^{153}$Sm-labelled BLCA-38 conjugate (6.00±2.19% ID/g). Moreover, blood pool activity was also lowest in this experimental group (0.23±0.06% ID/g) resulting in high xenograft:blood ratios (18.61±4.48).

Biodistribution of $^{153}$Sm-conjugates more closely resembled that of $^{111}$In-conjugates than that of $^{131}$I conjugates, in particular in relation to liver uptake. After injection of $^{153}$Sm-BLCA-38 of $^{111}$In-BLCA-38, liver uptake was 7.27±1.39% ID/g and 5.7±0.61% ID/g respectively, whereas after injection of $^{131}$I-BLCA-38, uptake in the liver was only 0.26±0.12% ID/g (Table 8). Total liver uptake of $^{153}$Sm-BLCA-38 at day 7 was 10.59±1.87% injected dose. The metal chelated MAbs also had a greater uptake than iodinated MAbs in the lung, spleen and kidneys.

The liver uptake demonstrated with the $^{153}$Sm-BLCA-38 conjugate appears to be a consequence both of a predilection of intact MAb to localise to liver following Fc receptor and lectin binding, together with our observation of colloid formation from the dissociation of $^{153}$Sm ions from the conjugate during incubation in plasma (see below).

A characteristic feature of the biodistribution of $^{153}$Sm-labelled conjugates was also noted in these studies, namely, the relatively high uptake in bone. Thus bone uptake was 2.11±0.37 and 2.70±0.32% ID/g after injection of either $^{153}$Sm-BLCA-38 or $^{153}$Sm-control respectively (Table 8). However, removal of the bone marrow demonstrated that it contained only 8% of the total bone activity indicating label deposition is mainly in osseous bone.

Animals injected with $^{153}$Sm-labelled MAbs had consistently higher blood clearance and liver uptake than animals injected with corresponding $^{111}$In- or $^{131}$I-labelled conjugates. To further understand the basis for this difference, plasma stability studies were undertaken (Table 9): $^{153}$Sm-BLCA-38 appears relatively stable when stored at RT, with less than 8% and 10% loss of label from the IgG at 24 and 48 h respectively. When incubated at 37° C. in plasma, the vast majority of radioactivity was still associated with the IgG (83 and 78% at 24 and 48 h respectively). However, a significant quantity was associated with both higher and lower molecular weight components, primarily colloid which was retained on a 0.02 micron filter.

A further feature of the biodistribution study above was enhanced blood clearance of the specific antibody compared to that of the control antibody of the same isotype regardless of the radiolabel that was used. One possible explanation for this finding is that the biodistribution of the specific MAb had been altered by the formation of immune complexes with antigen shed from the tumour. To investigate this point, a further series of nude mice which did not bear tumour xenografts were injected with $^{153}$Sm-BLCA-38. Biodistribution profiles were determined on day 7 and compared to the data obtained at this time in tumour-bearing animals (Table 10). These data confirmed that blood clearance of $^{153}$Sm-BLCA-38 was significantly faster in animals bearing a tumour xenograft than in non-tumour bearing animals (Blood uptake 0.23±0.06 and 1.30±0.41% ID/g respectively, P<0.02). Blood levels in mice without xenografts were comparable with those seen in tumour bearing mice injected with a control MAb (Table 8).

This study has shown that the anti-bladder cancer MAb, BLCA-38 will specifically localise to s.c. xenografts of the human BL-17 bladder cancer cell line when labelled with either $^{131}$I, $^{111}$In or $^{153}$Sm. Localisation was confirmed by scintigraphy (FIG. 11) in the case of the $^{131}$I-label, or by biodistribution (Table 8). This study also confirms that $^{153}$Sm labelled MAb distribution is characterised by increased liver uptake, rapid blood clearance and some skeletal retention of label.

EXAMPLE 10—Therapeutic effects of $^{153}$Sm-BLCA-38 on human cancer xenografts in nude mice Animals and xenografts Athymic BALB/c "nude" mice were maintained as in Example 9. Human cancer xenografts derived from the human bladder cancer BL-17 line described above or from Jo N, an ovarian cancer line developed as described by van Haaften-Day et al., 1988. The xenografted lines were maintained in serial passage as described by Russell et al. 1986. Tumours were measured at intervals using vernier callipers, and tumour volumes were determined from the formula for an ellipsoid (Russell et al. 1986).

Radiolabelling of monoclonal antibodies

Labelling of purified MAbs with $^{131}$I on $^{153}$Sm was carried out as described in Example 9.

Dosimetry

The radiation load on the tumour and other body organs from $^{153}$Sm-conjugated BLCA-38 was determined from biodistribution studies. Seven groups of 3 or 4 mice were killed from 30 min to seven days after the injection of $^{153}$Sm-BLCA-38 (150–175 μCi on 100 μg per mouse). Tissues were weighed and counted as described in Example 9. Activity per organ (or per gram tissue where the whole organ was not obtained) was expressed as a percentage of the initial injected dose of radioactivity and was plotted as a function of time. The cumulated activity for dose estimation was determined for each organ or for each gram of tissue as the area integrated under this curve plus an additional calculated component for those organs in which substantial activity was present at day 7. This component is given by cumulated activity for activity present at day 7:

$$= \frac{\text{activity present in organ}}{\lambda}$$

where $\lambda$ is the decay constant of $^{153}Sm$ $$= \frac{0.69147h - 1}{46.7}$$

The absorbed dose to each organ and to the xenograft was calculated as: A/m $\Sigma_i \Delta_i \Phi_i$ (Early and Sodee 1985) where A is the cumulated activity to the organ in μCi.h; m is the mean organ mass; $\Delta_i$ is the absorbed dose constant for the ith emission and $\Phi_i$ is the absorbed fraction for the ith emission. $^{153}$Sm is a beta emitter with $E_{max}$–640 (30%) 710 (50%) and 810 (20%) KeV. For this radioisotope, $\Sigma\Delta_i$ was taken as 0.5687 g rad/μCi.h (Myers et al. 1988) and $\Phi_i$ was assumed to be 1 for beta emissions in the small organs of mice. The absorbed dose from penetrating radiations in the mouse amounted to less than 2% of total body dosage based on the absorbed fractions and was therefore neglected.

Human Radiation Dose Estimate

Estimates of cumulated activity to human organs were obtained from comparisons of relative organ sizes (Feller and Sodd, 1975). Most murine organ masses were based on biodistribution data. Total blood mass was estimated at 5.85% of body mass and total skin, muscle, and bone masses were determined by dissection of two nude mice of appropriate body weight. The human organ mass to total body mass ratio was determined from figures published by Cloutier and Watson (1970) for blood, and by Snyder and co-workers (1974) for other tissues. Absorbed dosage from penetrating and non-penetrating radiation to the human organs were then determined using the DOSE program developed at ANSTO which is based on S-factors published by Snyder and co-workers. Activity in the blood was assigned where possible to blood-rich organs while the fraction of total radioactivity which could not be assigned to any particular organ was considered as total body activity.

Animal Studies (a) Short Term Effects of MAb Injection

Groups of up to 6 nude mice bearing human cancer xenografts of 200–1000 mm$^3$ were given a single i.p. injection of $^{153}$Sm-BLCA-38 or $^{153}$Sm-K-1-21 (control).

Approximately 100 µg of protein and 200–500 µCi was injected per animal. At this time tumour diameters were measured and the volume estimated. Seven days later tumour volumes were again determined and assessed as a percentage of the initial tumour volume. The mice were then killed and tumours were assessed for necrosis. As some patchy necrosis occurs spontaneously in large tumours, a "necrotic" tumour was defined as one which had become completely necrotic throughout its mass with virtually no intact xenograft tissue observable macroscopically.

Figure 12A:
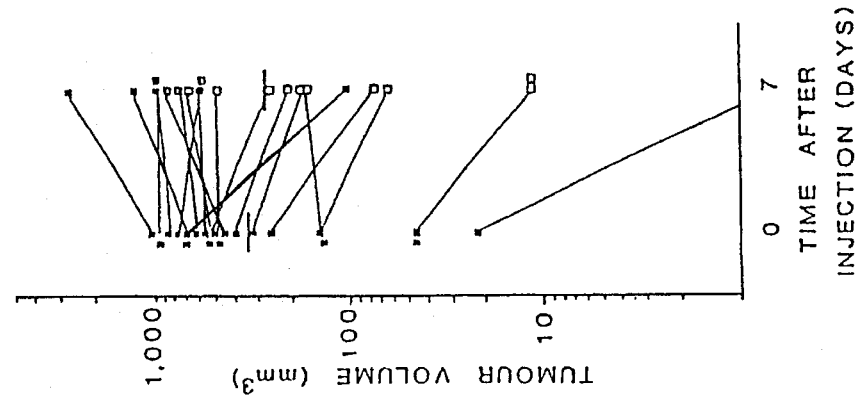

When mice bearing BL-17 human bladder cancer xenografts were treated in this way, the tumours grew 54% in geometric volume after injection of the control antibody. Three of the tumours (30%) showed no growth, while two had some necrosis. In contrast, mice injected with $^{153}$Sm-BLCA-38 showed an increase of only 25% geometric mean volume in the same period. Eight of the 15 tumours (53%) showed no growth while 7 (47%) had become completely necrotic. (FIG. 12A).

Figure 12B:
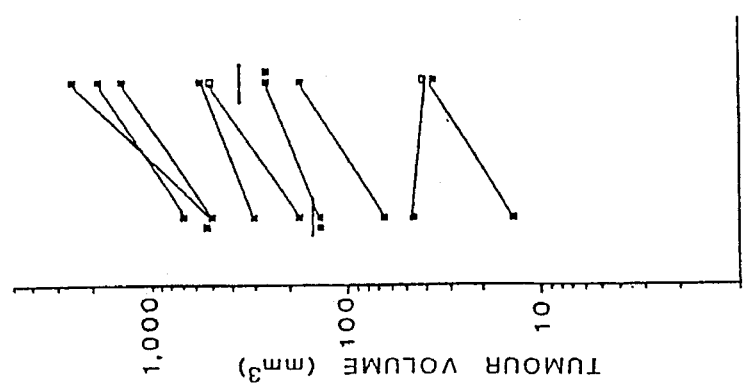
Figure 12C:
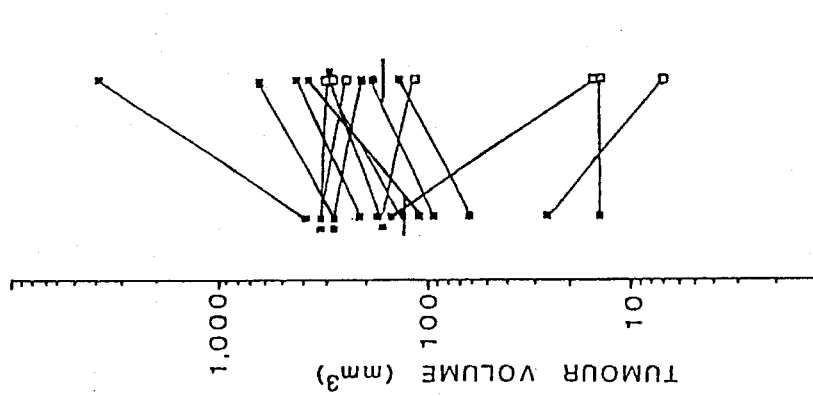
Figure 12D:
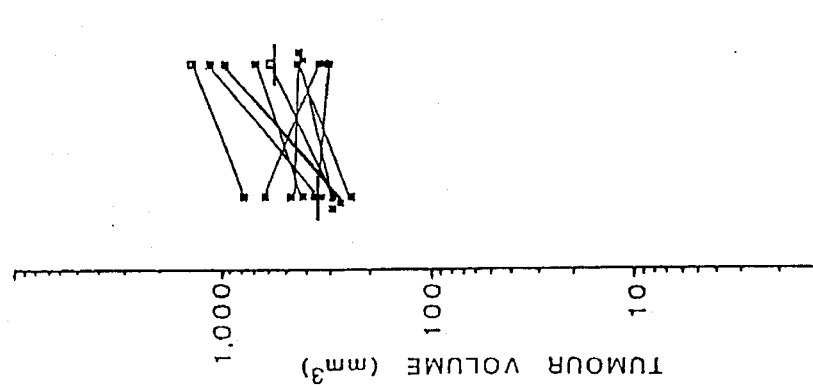

This study was repeated in mice bearing Jo. N. human ovarian xenografts (FIG. 12B). After injection of the control antibody, the tumours grew 132% in geometric mean volume. Only one (10%) failed to grow while 2 (20%) showed signs of necrosis. The mice injected with $^{153}$Sm-BLCA-38 showed a decrease of 13% in geometric mean volume. Fourteen of the 20 tumours (70%) failed to grow and 14 (70%) were completely necrotic. Both the failure to grow and the incidence of necrosis were significantly different between test and control groups (P<0.02 in each case $X^2$ test).

Long Term Effects of $^{153}$Sm-BLCA-38 Treatment

Figure 13A:
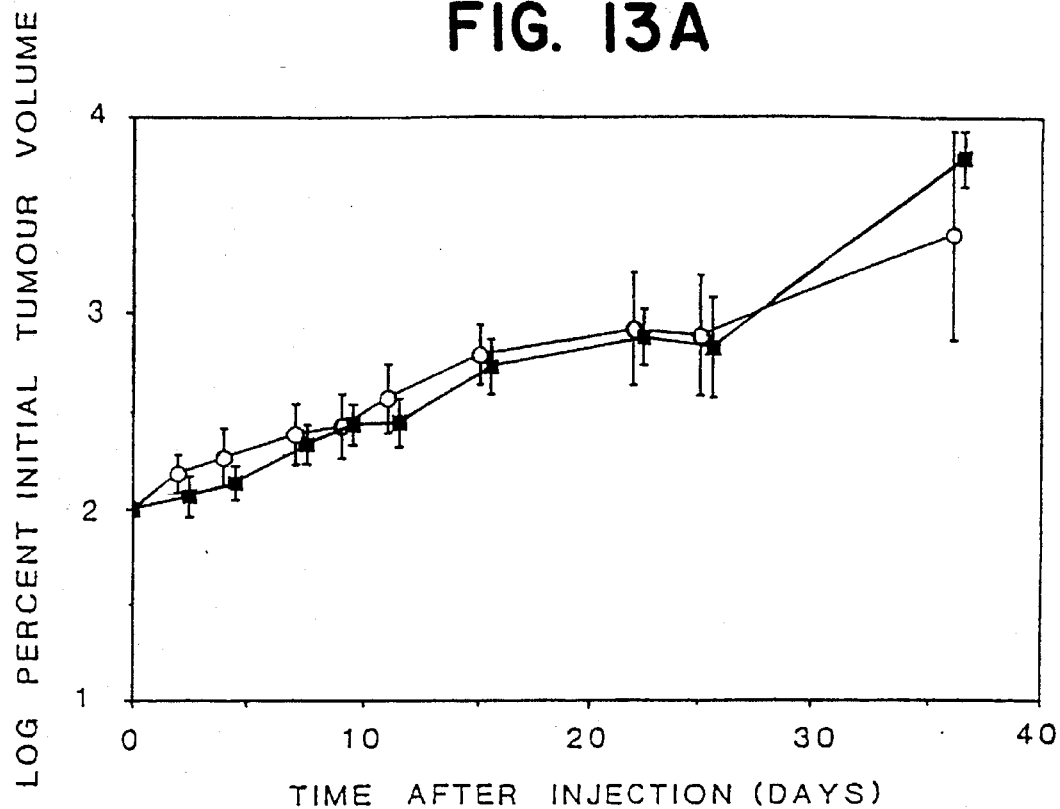

Three experiments were undertaken to determine if BLCA-38 either alone, or as a conjugate labelled with a beta emitting isotope, had any long term effects upon the growth of well established (200–1000 mm$^3$) BL-17 xenografts. Firstly, a comparison was made of the effects of unlabelled BLCA-38 and a control group injected with PBS (FIG. 13A). After the 36 day period of observation, mice injected with cold BLCA-38 had a mean log percent initial tumour volume of 3.4±0.53 which was not significantly different (Student's t-test) from that seen in animals injected with PBS (mean log percent initial tumour volume, 3.97±0.14).

Figure 13B:
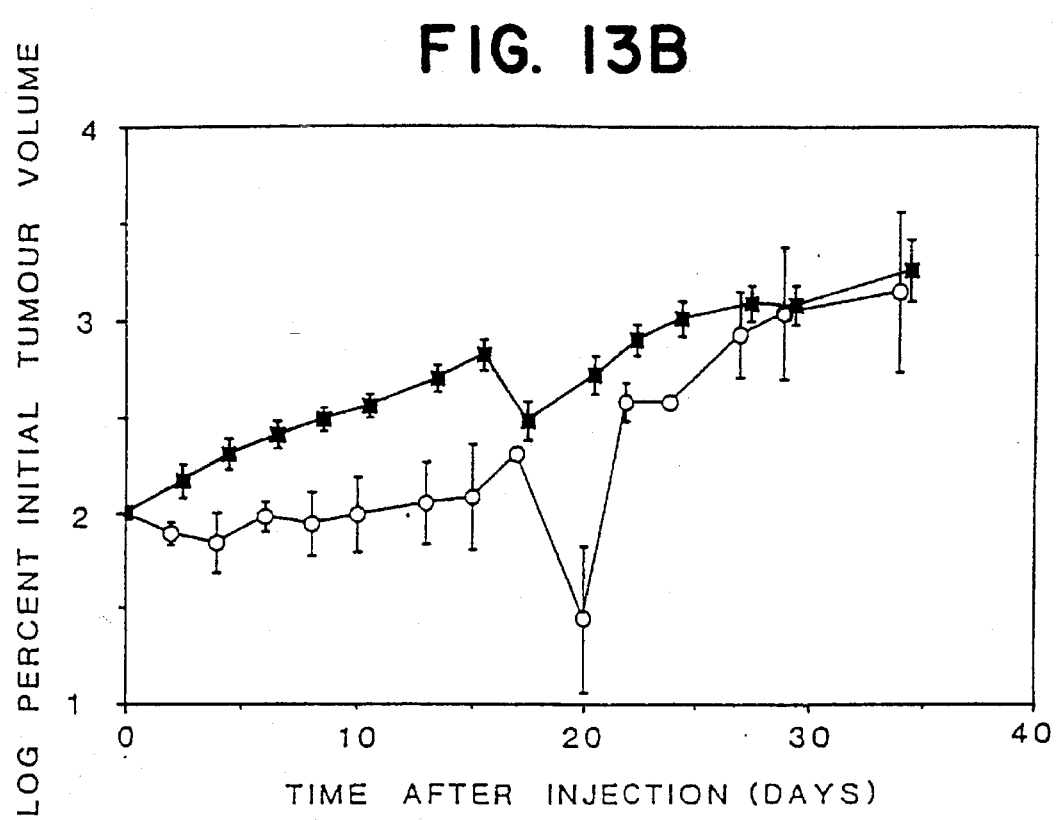

Secondly, the effect of injecting 500 µCi $^{131}$I-BLCA-38 or a $^{131}$I-control antibody was examined (FIG. 13B). For the first 25 days after antibody injection, there was a significant retardation in tumour growth in mice receiving $^{131}$I-BLCA-38 antibody compared with controls, with a dramatic fall in tumour volume at day 20. At this time there was also a decreased growth rate in mice receiving $^{131}$I-control MAb.

At day 20 the mean log percent initial tumour volume for treated mice was 1.44±0.38, compared with 2.72±0.10 in controls, (P<0.02, Student's t test). After this time there was a rapid recovery in growth rate so that by the end of the 36 day period of observation there was no difference in the mean log percent initial tumour volume of tumours in mice injected with $^{131}$I-labelled test (3.15±0.41) or control antibodies (3.26±0.16).

Figure 13C:
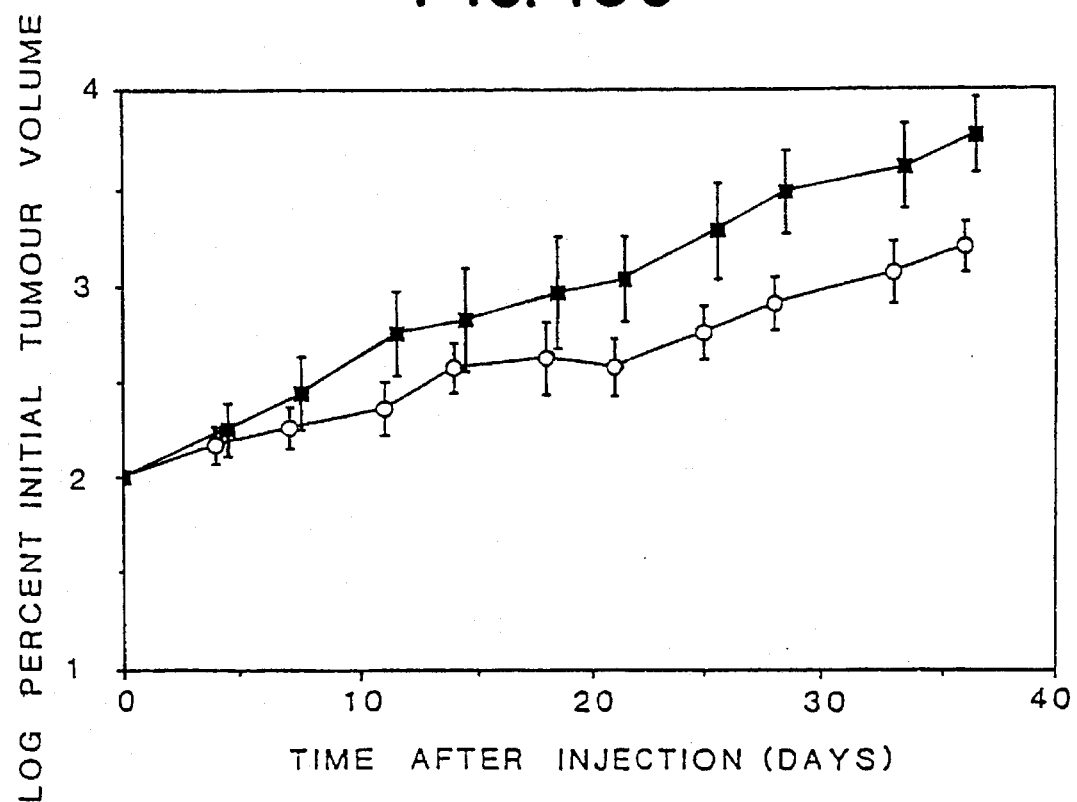

Thirdly, mice were injected with 250 µCi of $^{153}$Sm-labelled BLCA-38 or control MAb (these mice were given only half the dose given to mice receiving iodinated MAbs) (FIG. 13c). Tumours in mice which received $^{153}$Sm-BLCA-38 showed a steady growth rate which was consistently below that of the control group receiving $^{153}$Sm-labelled control antibody. This difference in growth rate became significant from day 21 onwards. At day 36 the mean log percent initial tumour volume of test animals was 3.19±0.13 and of controls was 3.77±0.19 (P<0.01).

It is of interest that the administration of $^{153}$Sm-MAb to tumour bearing nude mice did not induce excessive toxicity. Only one animal (receiving the control MAb) died and all others were thriving 40 days after $^{153}$Sm-MAb administration. These results can be compared with the use of Yttrium-90 labelled -MAb in nude mice bearing human colonic cancer xenografts (Sharkey et al. 1988). Despite a 75% tumour growth inhibition by 28 days, treatment was reported to be severely limited by bone marrow toxicity and single doses greater than 50 µCi could not be administered.

Dosimetric Studies

The radiation dosage to mouse organs and a BL-17 human bladder cancer xenograft was determined in nude mice injected i.p. with $^{153}$Sm-BLCA-38. Cumulative activities calculated are given in Table 11.

These calculations show that for a 1 mCi injection of $^{153}$Sm-BLCA-38, a radiation dose of the order of 2,000 rad would be given to the tumour. This compares favourably with all body organs except the liver and kidneys which would receive approximately 5,000 and 2,000 rads respectively. Significant radioactivity would also be received by bone, spleen, gonads and lungs.

The whole body dosage per mCi injected was determined from the total activities of all measured elements according to the MIRD dosage formula. Total cumulated activity to the body was 29,830 µCi.h, whilst body radiation does from beta radiation was 850 rads, whilst whole body radiation dose from gamma radiation (calculated from absorbed dose fractions) was 9.8 rads.

Biodistribution data obtained in nude mice were extrapolated to humans (Table 12). Most human organs showed a lower cumulated activity than their murine counterparts due to their lower percentage of total body mass.

TABLE 1

Summary of known reactivities for the panel of monoclonal antibodies

| Monoclonal | BLCA-8 | BLCA-30 | BLCA-38 |
|---|---|---|---|
| Reactivity* | | | |
| 1. Short term cultures | | | |
| a. Normal bladder | 0/1 | 0/0 | 0/1 |
| b. TCC bladder | 2/2 | 2/2 | 2/2 |
| 2. Human cancer cell lines | | | |
| bladder | 2/4 | 2/4 | 4/4 |
| Ovarian | 0/5 | 0/5 | 5/5 |
| Colonic | 0/4 | 0/4 | 3/4 |
| Melanoma | 0/5 | 0/5 | 2/5 |
| T lymphoid | 0/3 | 0/3 | 0/3 |
| B lymphoid | 0/10 | 0/10 | 0/10 |
| Leukemic | 0/2 | 0/2 | 0/2 |

*Number positive/number tested. ND indicates that an assay was not carried out.

TABLE 2

Reactivity or BLCA-8 with biopsy specimens

| Normal | | Other Bladder Conditions (Non-Malignant) | | Benign Conditions | | Carcinoma | |
|---|---|---|---|---|---|---|---|
| Bladder | 0/3* | Previous TCC | 2/4 | Bladder | 1/2 | Bladder | |
| Breast | 0/5 | Recurrent Infection | 2/5 | Ovary | 0/3 | TCC grade I | 6/6 |
| Testis | 0/2 | Chronic Inflammation | 0/2 | Prostate | 0/15 | TCC grade II | 7/7 |
| | | | | | | TCC grade III | 2/2 |
| Foetal Kidney | | Haematuria | 2/3 | | | Breast adenocarcinoma | 0/2 |
| 17 week | 1/1 | | | | | | |
| 14 week | 0/1 | | | | | | |
| Foetal Stomach | | | | | | Prostate adenocarcinoma | 0/2 |
| 17 week | 1/1 | | | | | | |
| 14 week | 0/1 | | | | | | |

*Number positive over number tested.

TABLE 3

Comparison of cytopathological findings with results of the monoclonal antibody assay of urine from TCC bladder patients

| | | | | MAb assay result | | | | | |
|---|---|---|---|---|---|---|---|---|---|
| Patient | TCC | TCC | Cytology | BLCA-8 | | BLCA-30 | | BLCA-38 | |
| No. | stage | grade | result | O* | I | O | I | O | I |
| 1** | T4 | 1–3 | Suspicious | ND | +++ | ND | +++ | ND | + |
| 2 | T4 | 3 | Positive | ND | +++ | ND | +++ | ND | ++ |
| 3 | T2 | 2 | Suspicious | +++ | +++ | +++ | +++ | ++ | + |
| 4 | T3 | 3 | Positive | − | ++ | − | + | − | − |
| 5 | T3 | 2–3 | Positive | ND | ++ | ND | − | ND | + |
| 6** | T3 | 3 | Negative | +++ | ++ | +++ | + | ND | − |
| 7 | T4 | 3 | Negative | ND | +++ | ND | +++ | ND | +++ |
| 8 | T3 | 2–3 | Positive | ++ | +++ | − | +++ | − | + |

*O: outer cells; I: inner cells
**patient in remission
ND Not done
− <5% positive cells
+ 5–9% positive cells
++ 10–19% positive cells
+++ >20% positive cells

TABLE 4

BLCA-8 reactivity of cells shed in voided urine from patients who had conditions other than biopsy-proven TCC of the bladder.

| Patient | Age/Sex | Condition | % BLCA-8 positive cells | |
|---|---|---|---|---|
| | | | inner | outer |
| A[a] | 50/F | Atypical cells in voided urine. Cystoscopy normal | ND[b] | 81 |
| B | 71/F | Cystectomy (previously treated for TCC) | 0 | 0 |
| B | 60/M | Cystectomy (previously treated for TCC grade III, $T_{is}/T_4$) | 0 | 0 |
| C[c] | 64/M | Biopsy showed inflammation only, previous TCC, grade III, $T_3$ | 67 | ND |
| D[d] | 58/M | Biopsy showed no evidence of disease (previous TCC, $T_3$) | 20 | 72 |
| E | 60/M | Degenerating cyst in kidney | 14 | ND |
| F | 28/F | Pyuria of unknown origin (query urinary tract infection) | 14 | ND |

[a]Also included in the normal population shown in FIG. 6
[b]Not done.
[c]Developed TCC, grade I–II. $T_a$ within 5 months
[d]Developed $T_{is}$ within 5 months

TABLE 5

Effects of enzymatic and chemical treatments on the cell surface expression of the BLCA-8 antigen

| Treatment | Cell Line | Percentage BLCA-8 positive cells | |
|---|---|---|---|
| | | Before Treatment | After Treatment |
| EDTA | BL-17 | 42 | 38 |
| 2-ME | BL-17 | 36 | 32 |
| pronase | BL-17 | 27 | 29 |
| fucosidase | BL-17 | 19 | 20 |
| neuraminidase | BL-23 | 80 | 88 |
| Limulus lectin | BL-23 | 91 | 94 |
| endoglycosidase F | BL-23 | 66 | 70 |
| periodate | BL-17 | 31 | 33 |

Human bladder cancer cells were treated with enzymes or chemicals before staining with BLCA-8 SN and SaMIg-FITC for surface immunofluorescence. Surface staining was analysed by flow cytometry.

TABLE 6

Effect of periodate or enzyme treatments on BLCA-8 antigen expression in a BL-23 lipid extract.

| Enzyme | Incubation Period | OD 405 nm untreated | OD 405 nm treated | Percentage change |
|---|---|---|---|---|
| 50 mM sodium periodate | 2 h | 0.988 | 0.986 | −0.2 |
| 25 mM sodium periodate | 2 h | 0.988 | 0.996 | −0.8 |
| β-galactosidase | 2 h | 0.925 | 1.539 | +66.0 |
| | 18 h | 0.784 | 1.845 | +135.0 |
| α-glucosidase | 18 h | 1.115 | 1.722 | +54.0 |
| β-glucosidase | 18 h | 1.115 | 1.227 | +10.0 |
| α-fucosidase | 18 h | 1.387 | 1.429 | +3.0 |

A lipid extract prepared from BL-23 human bladder cancer cells was bound to a solid phase and exposed to sodium periodate or various enzymatic treatments. BLCA-8 binding was then assessed by ELISA, using biotinylated BLCA-8 antibody followed by SA-AP. Colour development after addition of enzyme substrate was read at 405 nm.

TABLE 7

Staining of BLCA-8 reactive components in bladder cancer cell line lipid extracts, after thin layer chromatography.

| Reagent | Lipid Groups Detected | Staining of BLCA-8 reactive Components | |
|---|---|---|---|
| | | BL-17 extract | BL-23 extract |
| Anthrone | Glycolipids | + | ND[a] |
| Orcinol | Glycolipids | ND | + |
| Molybdenum Blue | Phospholipids | ND | + |
| Resourcinol | Gangliosides | ND | − |
| α-naphthol | Gangliosides Neutralglycolipids Sulfatides | ND | + |

[a]not done

TABLE 8

Tissue and xenograft activity in nude mice bearing BL-17 human bladder cancer xenografts seven days after injection of BLCA-38 or a control MAb labelled with 131-I, 111-In or 153-Sm. Results are expressed as percent injected dose per gram tissue plus or minus the standard error of the mean.

| Tissue* | $^{131}I$ | | $^{111}In$ | | $^{153}Sm$ | |
|---|---|---|---|---|---|---|
| | BLCA-38 | Control | BLCA-38 | Control | BLCA-38 | Control |
| X | 1.86 ± 0.75 | 1.02 ± 0.24 | 3.77 ± 0.24 | 4.05 ± 0.41 | 6.00 ± 2.19 | 3.33 ± 1.10 |
| BL | 1.59 ± 0.98 | 0.55 ± 0.23 | 1.42 ± 0.11 | 2.44 ± 0.35 | 0.82 ± 0.22 | 0.85 ± 0.17 |
| ST | 0.23 ± 0.60 | 0.17 ± 0.06 | 0.60 ± 0.05 | 0.67 ± 0.07 | 0.53 ± 0.17 | 1.04 ± 0.16 |
| SP | 0.93 ± 0.60 | 0.44 ± 0.17 | 2.57 ± 0.36 | 5.20 ± 0.47 | 1.74 ± 0.23 | 5.89 ± 1.78 |
| G | 0.29 ± 0.15 | 0.27 ± 0.08 | 1.07 ± 0.04 | 2.65 ± 0.49 | 1.70 ± 0.61 | 3.02 ± 0.86 |
| KD | 0.53 ± 0.31 | 0.47 ± 0.14 | 3.24 ± 0.17 | 3.68 ± 0.16 | 1.72 ± 0.31 | 2.06 ± 0.21 |
| LG | 1.26 ± 0.86 | 0.80 ± 0.25 | 1.25 ± 0.14 | 2.84 ± 0.15 | 0.78 ± 0.05 | 1.60 ± 0.38 |
| LV | 0.26 ± 0.12 | 0.37 ± 0.12 | 5.27 ± 0.61 | 5.33 ± 0.30 | 7.27 ± 1.39 | 7.33 ± 2.40 |
| MM | 0.21 ± 0.09 | 0.19 ± 0.04 | 0.37 ± 0.04 | 0.62 ± 0.06 | 0.19 ± 0.04 | 0.28 ± 0.03 |
| SK | 0.56 ± 0.28 | 0.29 ± 0.66 | 1.29 ± 0.15 | 2.53 ± 0.20 | 0.95 ± 0.25 | 1.22 ± 0.15 |
| B | 1.08 ± 0.68 | 0.27 ± 0.09 | 0.70 ± 0.10 | 1.76 ± 0.15 | 2.11 ± 0.37 | 2.70 ± 0.32 |
| BD | 1.59 ± 0.80 | 1.84 ± 0.60 | 0.92 ± 0.17 | 2.56 ± 0.28 | 0.23 ± 0.06 | 0.82 ± 0.17 |

*Abbreviations: X: xenograft; BL: bladder; ST: stomach; SP: spleen; G: gonad; KD: kidney; LG: lung. LV: liver; MM: muscle; SK: skin; B: bone; BD: blood.

TABLE 9

Stability of $^{153}$Sm-BLCA-38 as a stock solution or after incubation in murine plasma.

| | Time (hrs) | $^{153}$Sm-BLCA-38* | Percent Radioactivity | |
|---|---|---|---|---|
| | | | High MW species** | Low MW species |
| Stock | 0 | 96.1 | 1.9 | 2.0 |
| Solution | 3 | 95.8 | 3.2 | 1.0 |
| (RT) | 24 | 92.2 | 5.2 | 2.8 |
| | 48 | 90.7 | 8.1 | 1.2 |
| Plasma | 0 | 96.7 | 2.9 | 0.4 |
| (37° C.) | 3 | 87.6 | 10.8 | 1.6 |
| | 24 | 83.1 | 13.0 | 3.9 |
| | 48 | 77.0 | 16.5 | 6.5 |

*Retention time 8.6 min
**Combined filler retained and void volume component.

TABLE 10

Tissue and xenograft activity in nude mice bearing BL-17 human bladder cancer xenografts compared with mice without xenografts, seven days after injection of $^{153}$Sm-BLCA-38. Results are expressed as percent injected dose per gram tissue plus or minus the standard error of the mean.

| Tissue * | Xenograft | No Xenograft |
|---|---|---|
| X | 6.00 ± 2.19 | |
| BL | 0.82 ± 0.22 | 3.14 ± 0.31 |
| ST | 0.53 ± 0.17 | 3.69 ± 0.37 |
| SP | 1.74 ± 0.23 | 8.02 ± 0.45 |
| G | 1.70 ± 0.61 | 4.50 ± 0.59 |
| KD | 1.72 ± 0.31 | 4.36 ± 0.44 |
| LG | 0.78 ± 0.05 | 2.53 ± 0.39 |
| LV | 7.27 ± 1.39 | 12.56 ± 1.15 |
| MM | 0.19 ± 0.04 | 0.24 ± 0.05 |
| SK | 0.95 ± 0.25 | 1.44 ± 0.21 |
| B | 2.11 ± 0.37 | 2.88 ± 0.10 |
| BD | 0.23 ± 0.06 | 1.30 ± 0.41 |

*Abbreviations as in Table 8

TABLE 11

Estimate of Radiation Dosage to 11 Body Organs and a Bladder Cancer Xenograft in Nude Mice following a 1 mCi Intraperitoneal Injection of $^{153}$Sm-BLCA-38

| Tissue | A/g (µCi · hr/g) | Dose (rad) |
|---|---|---|
| Xenograft | 3357 | 1909 |
| Blood | 2718 | 1546 |
| Bladder | 1650 | 938 |
| Stomach | 860 | 487 |
| Spleen | 1910 | 1088 |
| Gonad | 2080 | 1185 |
| Kidney | 3860 | 2193 |
| Lung | 2050 | 1166 |
| Liver | 9190 | 5227 |
| Muscle | 313 | 178 |
| Skin | 916 | 521 |
| Bone | 2228 | 1267 |

TABLE 12

Estimation of Dosage to Human Organs following a 1 mCi injection of $^{153}$Sm-BLCA-38. These figures take into account Non-penetrating Radiation from within the Organ and Penetrating Radiation from the Surrounding Organs.

| Organ | Estimated Radiation Dosage (rad) |
|---|---|
| Bladder | 6.00 |
| Stomach | 0.16 |
| Spleen | 0.36 |
| Gonad | 0.39 |
| Kidneys | 0.64 |
| Lung | 0.39 |
| Liver | 1.64 |
| Muscle | 0.10 |
| Skin | 0.20 |
| Bone | 0.72 |
| Red Marrow | 0.53 |
| Yellow Marrow | 0.07 |
| Total Body | 0.19 |

References

Bender, N. H. Monoclonal antibodies in urologic oncology, Cancer, 60: 658 (1987)

Boniface, G R, Izard, M E, Walker, K Z, McKay, D R, Sorby, P J, Turner, J H, Morris, J G. The labelling of monoclonal antibodies with Samarium-153 for combined radioimmunoscintigraphy and radioimmunotherapy. J Nucl Med 30: 683 (1989).

Chopin, D K, deKernion J B, Rosenthal D L and Fahey J L. Monoclonal antibodies against transitional cell carcinoma for detection of malignant urothelial cells in bladder washing. J Urol. 134: 260 (1985).

Cloutier R J, Watson E E. Reaction dose from radioisotopes in the blood. In: *Medical Radionuclides: radiation dose and effects.* ORNLC 691212. Eds: Cloutier R J, Edwards C L, Snyder W S. Oak Ridge National Laboratory, OaK Ridge pp 325–346 (1970).

Early P J and Sodee D B Dosimetry. In *Principles and Practice of Nuclear Medicine* pp 113–130 CV Mosby Co, Toronto (1985).

Edwards, P. A. W., Smith C. M., Neville A. M. and O'Hare M. J. A human-human hybridoma system based on a fast-growing mutant of the ARH-77 plasma cell leukaemia-derived line Eur. J. Immunol 12: 641 (1982). Feller P A and Sodd V J. Dosimetry of four heart imaging radionuclides: 43K, 81Rb, 129 Cs and 201 TlJ. Nucl Med Inst. Phys. 16: 1070 (1975).

Hakomori, S. Tumor-associated carbohydrate antigens Ann. Rev. Immunol., 2: 103 (1984).

Huland H, Otto U and Droese M. The value of urinary cytology, serum and urinary carcinoembryonic antigen, rheumatoid factors and urinary immunoglobulin concentration as tumour markers or diagnostic factors in predicting progression of superficial bladder cancer. Eur Urol. 9 346 (1983).

Kohler G and Milstein C. Derivation of specific antibody-producing tissue culture and tumour lines by cell fusion, Eur J Immunol 6: 511 (1976)

Leeden R W and R K Yu 1982 Gangliosides: structure, isolation and analysis Meth. Enzymol 83: 139–191.

Limas C and Lange P. altered reactivity for A,B,H antigens in transitional cell carcinomas of urinary bladder. A study of the mechanisms involved. Cancer 46: 1366 (1980).

Longin, A, Hijazi, A, Berger-Dutrieux, N, Escourrou, G, Bouvier, R, Richer, G, Mironneau, I, Fontaniere, B, Devonec, M and Laurent, J C. A monoclonal antibody (BL2-10DI) reacting with a bladder cancer-associated antigen. Int. J. Cancer, 43: 183, (1989).

Magnani, J L, Brockhaus, M, Smith, D F, Ginsburg, V, Blaszczyk, M, Mitchell, K F, Steplewski, Z and Koprowski, H—A monosialoganglioside is a monoclonal antibody-defined antigen of colon carcinoma. Science, New York, 212: 55–56, 1981.

Masuko, T, Yagita, H and Hashimoto, Y Moncolonal antibodies against cell surface antigens present on human urinary bladder cancer cells. J. Nat. Cancer Inst., 72: 523 (1984).

McCabe, R P, Haspel, M V, Potamo, N and Hanna, M G. Monoclonal antibodies in the detection of bladder cancer. In: H Z Kupchik (Ed.), *Cancer Diagnosis in Vitro using Monoclonal Antibodies*, pp. 1–29, Marcel Dekker Inc. New York (1988).

Murphy W M, Soloway M S, Jukkola A F, Crabtree W N and Ford K S. Urinary cytology and bladder cancer. The cellular features of transitional cell neoplasms cancer 3: 1555 (1984).

Piccoli G, Varese D and Rotienno M. Diagnosis and clinical correlations in Nephrology In: *Atlas of Urinary Sediments*, Raven Press, New York pp 48–49 (1984).

Ridell, M, Minnikin, D E, Parlett, J H and Mattsby-Baltzer, I. Detection of mycobacterial antigens by a combination of thin-layer chromatography and immunostaining. Lett. App. Microbiol. 2: 89 (1986)

Russell P J, Raghavan D, Philips J and Wills E J. The biology of urothelial cancer In: *The Management of Bladder Cancer* Ed D Raghavan, Edward Arnold Publishers, London pp 1–41 (1988a).

Russell P. J. Wass J, Lukeis R, Gibson M, Jelbart M, Wills E, Phillips J, Brown J, Carrington N, Vincent P and Raghaven D, Characterisation of cell lines derived from a multiply aneuploid human bladder transitional cell carcinoma. UCRU-BL-13. Int J Cancer 44: 1 (1989)

Russell, P. J. Wills, E. J. Phillips, J. Jelbart, M. Gregory, P. Raghavan, D-Features of squamous adenocarcinoma in the same cell in a xenografted human transitional cell carcinoma: Evidence of a common histogenesis? Urol Res 16: 79 (1988b).

Russell, P J, Raghaven D, Gregory, P, Philips, J, Wills, E J, Jelbart, M, Wass, J, Zbroja, R, Vincent, P G. Bladder cancer xenografts: a model of tumour cells heterogeneity. Cancer Res 46: 2035. (1986).

Sharkey, R M, Kaltovich F A, Shih L B, Fand I Govelitz G, Goldenberg O M. Radioimmunotherapy of human colonic cancer xenografts with 90Y-labeled monoclonal antibodies to carcinoembryonic antigen. Cancer Res 48: 3270 (1988)

Snyder W S, Ford M R, Warner G G, Watson S B. A tabulation of dose equivalent per microcurie-day for source and target organs of an adult for various radionuclides. In: ORNL-500, Oak Ridge National Laboratory, Oak Ridge p 3 (1974).

Sonino, S, Ghidoni, R, Gazzotti, G, Acquotti, D, and Tettamanti, G. New trends in ganglioside chemistry. In: A M Wu and L G Adams (eds), *The Molecular Immunology of Complex Carbohydrates*, pp 437–464, Plenum Press, New York. (1988).

Svennerholm, L. The ganglioside. J. Lipid Res., 5: 145–155, 1964.

Van Haaften-Day C, Russell, P, Carr, S, Wright, L. Development and characterisation of a human cell line from an ovarian mixed mullerian tumour (carcinosarcoma). *In Vitro* Cell Dev Biol 24: 965 (1988)

Vardal F, Vandvik B and Lea T. Immunofluorescence staining of agarose-embedded cells: A new technique developed for immunological characterisation of markers on a small number of cells. J Immunol Meth. 92: 125 (1986)

Walker K Z, Gibson J, Axiak S M and Prentice R L Potentiation of hybridoma production by the use of mouse fibroblast conditioned media. J Immunol Methods 88: 75 (1986)

Walker, K Z, Seymour-Munn, K, Keech, F K, Axiak, S M, Bautovich, G J Morris, J G, Basten, A. A rat model system for radioimmunodetection of kappa myeloma antigen on malignant B cells. Eur J Nucl Med 12: 461 (1986).

Ward E S, Gussan D, Griffiths A D, Jones P T and Winter G, Nature 341 544 (1989)

Zola, H, Moore, H A, Hunter I K, and Bradley, J. Analysis of chemical and biochemical properties of membrane molecules in situ by analytical flow cytometry with monoclonal antibodies. J. Immun. Meth, 74: 65 (1984a).

Zola, H, Moore, H A, Hinter, I K, Nikoloutsopoulos, A, and Bradley, J. The antigen of mature human B cells detected by the antibody FMC7: studies of the nature of the antigen and modulation of its expression. J. Immunol. 133: 321 (1984b).

We claim:

1. A hybridoma cell line producing an antibody directed against an antigen of malignant cells associated with transitional cell carcinoma of the human bladder, which antigen is found in voided urine of transitional bladder cell carcinoma patients, characterized in that the hybridoma cell line is selected from the group consisting of HB10406, HB11784 and HB11785.

2. A cell-line according to claim 1, wherein the hybridoma cell line is HB10406.

3. A cell line according to claim 1, wherein the antigen found in the voided urine of the patient is stable in the voided urine of the patient.

4. A cell line according to claim 1, wherein the cell line secretes an antibody or single domain antibody which recognizes a transitional bladder carcinoma cell line selected from UCRU-BL-17-CL, UCRU BL-23/3, UCRU-BL-13/0 and 5637.

5. A cell line according to claim 1, produced by the fusion of an antibody-producing cell with a myeloma cell.

6. A cell line according to claim 1, wherein the antigen is a lipid, or carbohydrate.

7. A cell line according to claim 1, wherein the antigen is a neutral glycolipid.

8. A cell line according to claim 1, wherein the antigen is a carbohydrate.

9. An antibody or a single domain antibody reactive with an antigen of malignant cells associated with transitional cell carcinoma of the human bladder, which antigen is found in voided urine of transitional bladder cell carcinoma patients, wherein the antibody or single domain antibody is produced by a cell line according to claim 1.

10. A monoclonal antibody reactive with transitional cell carcinoma of the human bladder, wherein the monoclonal antibody is produced by a hybridoma cell line selected from the group consisting of HB10406, HB11784 and HB11785.

11. A monoclonal antibody according to claim 1, wherein the monoclonal antibody is produced by the hybridoma cell line HB10406.

12. An antibody according to claim 10, wherein the antibody is in labelled form.

13. An antibody according to claim 12, wherein the label is selected from an enzyme, a fluorescent label, a radio label or a second antibody against the first antibody in labelled form.

14. An antigen-binding fragment or portion of an antibody according to claim 10, which antigen-binding fragment or portion is reactive with malignant cells associated with transitional cell carcinoma of the human bladder and recognizes an antigen found in the voided urine of transitional bladder cell carcinoma patients.

15. An antibody composition comprising at least one antibody according to claim 10 together with a pharmaceutically acceptable carrier or diluent.

16. An antibody composition according to claim 15 wherein the antibody is in labelled form.

17. An antibody composition comprising at least one antigen binding fragment or portion of an antibody according to claim 10, together with a pharmaceutically acceptable carrier or diluent.

18. A hybridoma cell line which produces an antibody to an antigen of malignant cells associated with transitional cell carcinoma of the human bladder, wherein the cell line is selected from the group consisting of HB10406, HB11784 and HB11785; and wherein the antigen is found in voided urine from transitional bladder cell carcinoma patients, and wherein the time required for the amount of the antigen in the urine to decrease by one-half is at least 18 hours.

19. The cell line according to claim 18, wherein the time required for the amount of the antigen in the urine to decrease by one-half is at least 12 hours.

20. The cell line according to claim 18, wherein the time required for the amount of the antigen in the urine to decrease by one-half is at least 8 hours.

21. A cell producing an antibody or a single domain antibody directed against an antigen of malignant cells associated with transitional cell carcinoma of the human bladder, wherein the antigen is found in voided urine of transitional bladder cell carcinoma patients, characterized in that the cell line expresses an antibody or a single domain antibody that binds to the same transitional cell carcinoma epitope as is bound by an antibody expressed by a hybridoma cell line selected from the group consisting of HB10406, HB11784 and HB11785.

22. An antigen-binding fragment or portion of an antibody or a single domain antibody according to claim 9, wherein the antigen-binding fragment or portion is reactive with malignant cells associated with transitional cell carcinoma of the human bladder and recognizes an antigen found in the voided urine of transitional bladder cell carcinoma patients.

23. A cell line according to claim 21, wherein said hybridoma cell line is HB10406.

24. A cell line according to claim 21, wherein said hybridoma cell line is HB11784.

25. An antibody or a single domain antibody according to claim 9, wherein cell line is HB10406.

26. An antibody or a single domain antibody according to claim 9, wherein cell line is HB 11784.

* * * * *